US012691144B2

(12) United States Patent
Ferrari et al.

(10) Patent No.: US 12,691,144 B2
(45) Date of Patent: Jul. 28, 2026

(54) OVOTRANSFERRINS FOR USE IN THE TREATMENT OF IRON DEFICIENCY ANAEMIA

(71) Applicant: BIOSEUTICA B.V., Zeewolde (NL)

(72) Inventors: Valerio Maria Ferrari, Milan (IT); Maria Carla Baggio, Saronno (IT); Paride Grisenti, Milan (IT)

(73) Assignee: BIOSEUTICA B.V., Zeewolde (NL)

( * ) Notice: Subject to any disclaimer, the term of this patent is extended or adjusted under 35 U.S.C. 154(b) by 319 days.

(21) Appl. No.: 18/546,979

(22) PCT Filed: Feb. 21, 2022

(86) PCT No.: PCT/EP2022/054185
§ 371 (c)(1),
(2) Date: Aug. 18, 2023

(87) PCT Pub. No.: WO2022/175509
PCT Pub. Date: Aug. 25, 2022

(65) Prior Publication Data
US 2024/0148837 A1 May 9, 2024

(30) Foreign Application Priority Data
Feb. 22, 2021 (EP) ..................................... 21158368

(51) Int. Cl.
| *A61K 38/40* | (2006.01) |
| *A61K 33/26* | (2006.01) |
| *A61P 3/02* | (2006.01) |

(52) U.S. Cl.
CPC .............. *A61K 38/40* (2013.01); *A61K 33/26* (2013.01); *A61P 3/02* (2018.01)

(58) Field of Classification Search
None
See application file for complete search history.

(56) References Cited

U.S. PATENT DOCUMENTS

2015/0087582 A1* 3/2015 LoVetri ................... A61P 43/00
514/2.4

FOREIGN PATENT DOCUMENTS

| CN | 1850270 A | * 10/2006 |
| EP | 0537634 A2 | 4/1993 |

OTHER PUBLICATIONS

Rathnapala et al. Functional properties of ovotransferrin from chicken egg white and its derived peptides:a review: Mar. 29, 2021.*

Galla et al. "Ovotransferrin Supplementation Improves the Iron Absorption: An In vitro Gastro-Intestinal Model" Oct. 2021.*

Galla R. et al., "Ovotransferrin supplementation improves the iron absorption: an in vitro gastro-intestinal model", Biomedicines, vol. 9, No. 11, Nov. 26, 2021, p. 1543.

Ko K.Y. et al., "An economic and simple purification procedure for the large-scale production of ovotransferrin from egg white", Poultry Science, vol. 87, No. 7, Jul. 1, 2008, pp. 1441-1450.

Lun Lung N et al., "Calorimetric studies of serum transferrin and ovotransferrin. Estimates of domain interactions, and study of the kinetic complexes of ferric ion binding", Biochemistry, vol. 33, No. 7, Feb. 22, 1994, pp. 1881-1888.

Mason J., "Effects of conalbumin bound iron on the growth of *Salmonella paratyphi* B and *Salmonella thompson*", Portland State University, Jan. 1, 2000, retrieved from the internet: URL: https://pdxscholar.library.pdx.edu/cgi/viewcontent.cgi?article-5426&context=open_access.etds.

Search Report and Written Opinion of PCT/EP2022/054185 of Jun. 13, 2022.

Thompson D. B., "Iron binding by ovotransferrin from ferric nitrilotriacetate at pH 5 and pH 5.5", Journal of Food Science, vol. 53, No. 3, May 1, 1988, pp. 929-931.

Valenti P. et al., "The effect of saturation with Zn2+ and other metal ions on the antibacterial activity of ovotransferrin", Medical Microbiology and Immunology, vol. 176, No. 3, Apr. 1, 1987, pp. 123-130.

* cited by examiner

*Primary Examiner* — Danah Al-Awadi
(74) *Attorney, Agent, or Firm* — Silvia Salvadori, P.C.; Silvia Salvadori

(57) ABSTRACT

Ovotransferrins with a degree of iron saturation from 0 to 15% are useful in the treatment of iron deficiency and iron deficiency anaemia, increasing the cell viability on gastric and intestinal cell models with respect to the holo-OvT 100%, when tested at the same concentrations, showing also a surprisingly better time dependent absorption of iron ions and a physiological trend allowing a single oral administration in 24 hours.

5 Claims, 18 Drawing Sheets

GTL-16 cells

CaCo2 cells

GTL-16 cells,

CaCo2 cells

3D GASTRO-INTESTINAL MODEL

DMT-1

Ferroportin

Caco-2 cells

*Ferritin*

*Ferroportin*

A

B

OVOTRANSFERRINS FOR USE IN THE TREATMENT OF IRON DEFICIENCY ANAEMIA

This application is a U.S. national stage of PCT/EP2022/054185 filed on 28 Jan. 2022, which claims priority to and the benefit of European Patent Application No. 21158368.7 filed on 22 Feb. 2021, the contents of which are incorporated herein by reference in their entireties.

The present invention concerns ovotransferrins with a degree of iron saturation from 0 to 15% for use in the treatment of iron deficiency and iron deficiency anaemia, as well as compositions comprising said ovotransferrins.

BACKGROUND OF THE INVENTION

Iron is an essential element for the maintenance of a myriad of body functions, particularly involved in the production of haemoglobin, the molecule that carries oxygen in the blood, necessary to maintain healthy cells, skin, hair, and nails. Iron ions, naturally present in foods and beverages, are absorbed into the body by the cells lining the gastrointestinal tract. It is not possible to generalize the exact percentage of iron that is absorbed from the diet, it is suggested that approximately 10%-20% of an oral iron dose is absorbed (Goroll A H, Mulley A G. *Office evaluation and management of the adult patient*. Primary Care Medicine. Chapt 82:607-608). The absorbed fraction is then released into the blood stream, where a transferrin, a glycoprotein present in biological fluids, attaches to it and delivers the iron to the liver as ferritin, a globular protein present in every cell type (Theil E C (1987). "*Ferritin: structure, gene regulation, and cellular function in animals, plants, and microorganisms*". Annual Review of Biochemistry. 56 (1): 289-315) and released as needed to make new red blood cells in the bone marrow. When red blood cells are no longer able to function (after about 120 days in circulation), they are re-absorbed by the spleen and the iron from these old cells can also be recycled by the body. Iron deficiency is very common, especially among women in the fertile period (women who menstruate, pregnant and breastfeeding) and in postmenopausal women (K. Qamar et al. *Malabsorption of iron as a cause of iron deficiency anemia in postmenopausal women*; Pak J Med Sci. 2015 March-April; 31(2): 304-308) or in subjects who have undergone major surgical of physical trauma or with gastrointestinal diseases (i.e. celiac disease, inflammatory bowel disease, ulcerative colitis, Chron disease and peptic ulcer disease) and in people who have a diet that is low in iron, like vegetarians whose diet do not include iron-rich foods since it is known that iron from vegetables is not absorbed as well as iron from meat, poultry and fish (heme-iron). Iron-deficiency (ID) is defined as the decrease of the total content of iron in the body. Iron deficiency anaemia (IDA) occurs when ID is sufficiently severe to reduce erythropoiesis. They are diagnosed by blood tests that include the blood count, the levels of serum ferritin, iron, total iron-binding capacity, and transferrin. Anaemia resulting from iron-restricted erythropoiesis occurs through several mechanisms: in pure iron deficiency, depleted iron stores are due to an imbalance between iron uptake and utilization. The persistence of a negative iron balance leads to microcytic (red bloods cell are smaller than normal) and hypochromic (red bloods cells have less haemoglobin than normal) anaemia. In these cases, an adequate iron repletion and management of the cause of iron deficiency led to resolution. It is important to assure a prompt treatment in patients with iron deficiency anaemia (IDA) since a proper management may improves quality of life, alleviates the symptoms of iron deficiency (like fatigue, paleness, shortness of breath, headaches, heart palpitation, etc.), possible cognitive deficits and reduces the need for blood transfusions. The management of moderate iron deficiency anaemia may be done by administration of iron ions: this simple treatment can be done by oral administration of ferrous sulphate 200 mg (65 mg iron) twice daily even if lower doses may be as effective and better. In fact, up to 30% of patients experience dose limiting side effects with ferrous ions supplementation due to gastrointestinal side effects such as epigastric discomfort, nausea, vomiting, diarrhoea, constipation, abdominal colicky pain and dark stools. Other iron compounds (e.g. ferrous fumarate, ferrous gluconate) or formulations (iron suspensions) may also be tolerated better than ferrous sulphate but still presenting undesired side effects such as nausea, vomiting, diarrhoea, metal odour, etc., and even iron poisoning (ingestion of doses of elemental iron higher than 35 milligrams per kilogram of body weight may be fatal in children).

Oral iron treatment should be continued for 3 months after the iron deficiency has been corrected so that stores are replenished. More recently review on pregnant women with IDA, showed that the daily oral administration of bovine lactoferrin (bLact) is just as good as ferrous sulfate in improving hematological parameters (increasing Hb, serum ferritin and iron levels) with fewer gastrointestinal side effects (H. A. Hashim et al. *Lactoferrin or ferrous salts for iron deficiency anaemia in pregnancy: A meta-analysis of randomized trials* 219, 45-52, Dec. 1, 2017). bLact is a glycoprotein from transferrin family present in high concentrations in milk of humans and other mammals, this molecule showed an isoelectric point of 8,1, has twice higher affinity for iron than human serum transferrin and it is able to reversibly chelates two $Fe^{+3}$ ions per molecule. In the above cited review of Hashim, the administration of 100 mg of bovine lactoferrin twice a day before meals for four weeks is equivalent to the administration of 100 mg of elemental iron. CN1850270 discloses the use of another iron binding glycoprotein belonging to the family of transferrin., namely ovotransferrin (holo OvT) saturated with trivalent iron ions as iron supplement/fortification, wherein the molar ratio of ovotransferrin and iron ions in the complex is 1:0.5-2, which corresponds to a degree of iron saturation of OvT ranging from 100% to 25%. This degree of iron saturation of hen egg ovotransferrin tested on an animal model (Kunming mice) showed a potential therapeutic use for treating iron deficiency. These experimental tests were carried out on a crude OvT powder and not on a pure compound since the described purification processes from hen egg white (filtration, dialysis and ultrafiltration) are not able to afford a purified product being not able to remove other ovoproteins with similar molecular weight. OvT (also known as conalbumin) is an egg white glycoprotein responsible for the transfer of ferric ions from the hen oviduct to the developing embryo. This compound consists of a 686 amino acids single polypeptide chain with a molecular mass of about 78-80 kDa and a single glycan chain (composed of mannose and N-acetylglucosamine residues) in the C-terminal domain (G. Spik et al., 1988, *Comparative study of the primary structures of sero-, lacto- and ovotransferrin glycans from different species*. Biochimie 70:1459-1469) and shows an isoelectric point of 6.0. OvT is synthesized in the hen oviduct and deposited in the albumen fraction of eggs and represents about 12%-13% of total egg white proteins. OvT contributes to promoting the growth and development of the chicken embryo mainly preventing the growth of micro-organisms together with other proteins such as lysozyme (Deeming, D. C. *Behavior patterns during incubation*. In Avian Incubation: Behaviour, Environment, and Evolution; Deeming, D. C., Ed.; Oxford University Press: Oxford, U K, 2002; pp. 63-87), cystatin (Saxena, I.; Tayyab, S. *Protein proteinase inhibitorsfrom avian egg whites*. Cell. Mol. Life Sci. 1997, 53, 13-23), ovomacroglobulin (Miyagawa, S et al., *Spreading of Serratia marcescens in experimental keratitis and growth suppression by chicken egg white ovomacroglobulin*. Jpn. J. Ophthalmol. 1991, 35, 402-410) and avidin (Board, P. A.; Fuller, R. *Non-specific antimicrobial defences of the avian egg, embryo and neonate*. Biol. Rev. Camb. Philos. Soc. 1974, 49, 15-49). Similarly to other transferrins, OvT is a two lobed protein, and possesses the capability to reversibly bind two $Fe^{3+}$ ions per molecule, along with two $CO_3^{2-}$ or $HCO_3^-$ ions, with high affinity, thus delivering iron into host cells by membrane-bound specific receptors (AB Mason et al.; (1996) *Association of the two lobes of ovotransferrin is a prerequisite for receptor recognition. Studies with recombinant ovotransferrins*. Biochem J 15:361-368). The potential use of OvT as nutritional ingredient is under investigation (F. Giansanti et al.; *The Nutraceutical Properties of Ovotransferrin and Its Potential Utilization as a Functional Food*, Nutrients 2015, 7, 9105-9115). OvT appears in two forms: apo-form and holo-form. The apo-OvT form does not contain iron while the holo-form may contain up to about 1.4 mg of iron/g of protein (100% saturated); the holo OvT forms seems more stable to proteolytic hydrolysis and to heat denaturation (Thomas J. W et al., *The primary structure of hen ovotransferrin*. European Journal of Biochemistry. 1982; 122(2):2297-2303; U.S. Pat. No. 8,227,207). More recently OvT (unspecified holo and apo form) is under clinical evaluation in COVID19 patients as an immuno-modulator in addition to the standard of care therapy (ClinicalTrials.gov Identifier: NCT04643054).

The potentiality of OvT as dietary supplementation for treating IDA seems associated to OvT holo forms in which the degree of saturation ranges from 100% (2 moles of iron per molecule of OvT) and 25% (0.5 molecules of iron per molecules of OvT), as disclosed in CN 1850270, but the biochemical and clinical evidence of the effectiveness to use OvT with the above-mentioned degree of saturation in treating IDA was not really proved as well as the efficacy of OvT apo form or OvT a very low degree of iron saturation. Moreover, the isoelectric point of OvT (i.e. 6,0) suggested that in an acidic environment, like those represented "in vivo" by the gastric juices, the stability of the holo OvT form is compromised releasing "one pot" the iron salts in the stomach and therefore limiting the possibility to reduce the above described side effects usually associated to the administration of the inorganic and organic iron salts already utilized in therapy or as iron supplementation (S. Abeyrathne et al., *Separation of Ovotransferrin from Chicken Egg White without Using Organic Solvents*, Iowa State University Animal Industry Report 2015; Okamoto, K et al.; *Iron-Binding Process in the Amino- and Carboxyl-Terminal Lobes of Ovotransferrin: Quantitative Studies Utilizing Single Fe3+-Binding Mutants* Biochemistry 2004, 43, 34, 11118-1112).

Ko K. Y. et al., Poutry Science. Vol 87, no 7, Jan. 7, 2008, 1441-1450, studied the iron binding capacity of whole egg white: no conclusive information on the correlation between pH and degree of iron saturation of pure ovotransferrin could be deduced from this study, carried out on whole egg white.

Mason John, "Effects of conalbumin bound iron on the growth of S. thyphimurium and S. thompson", Portland State University, 1.1.2020, XP 055827266, discloses the preparation of mixtures of apo ovotransferrin and holo ovotransferrin for use in microbial broth medium. The degree of iron saturation was determined on the mixture and not on real homogeneous ovotransferrin.

EP 0537634 discloses iron complexes with conalbumin and its derivatives selected from the group consisting of acetylconalbumin and succinylconalbumin, with iron content ranging from 2 to 30% by weight, exceeding the 100% iron saturation degree of ovalbumin (about 1400 ppm).

Thompson Donald B. et al., Journal of Food Science, vol 53, No. 3, 1.5.1988, 929-931, discloses the tests carried out on crude hen egg white (Table 1) in which the presence of ovotransferrin is, according to the same authors, only 1,3% in mixture with other ovoproteins. The reported degree of saturation of purified ovotransferrin at pH 5.26 (Table 2) is 53%.

Lin Lung Nan et al., Biochemistry, Vol 33., no.7, 22.2.1994, 1881-1888, report a different trend between the degree of iron saturation and pH values. The DSC thermograms of FIG. 5 were obtained at intermediate level of saturation, whereas the maximum value of iron saturation is obtained at pH 6.3 (=0.99 sites) and the lower value of iron saturation is obtained at pH 7.5 (=0.44 sites). The correlation between pH and degree of iron saturation for ovotransferrin was not experimentally demonstrated.

There is therefore the necessity to reduce the side effects of the traditional ID and IDA therapies and more in particular to develop a more controlled and absorption of the iron ions, focused to avoid any excess of unbonded iron ions.

DESCRIPTION OF THE INVENTION

It has now been found that apo-ovotransferrin (apo-OvT) and holo-ovotransferrin with a low content of iron, from 1-10 ppm to 201-256, preferably 221-227 ppm provide significant advantages as iron supplements and iron absorption enhancers in comparison with holo-ovotransferrin having an iron content of about 1490 ppm, corresponding to a saturation degree of 100% (holo-OvT 100%), and to bovine lactoferrin (bLact). The advantageous effects of apo-ovotransferrin (apo-OvT) and holo-ovotransferrin with a degree of iron saturation between 0.5 and 15% have been evidenced in in vitro gastric and intestinal models as well as in a three-dimensional (3D) validated in-vitro model mimicking in vivo complexity of the gastro-intestinal barrier. Apo-ovotransferrin (apo-OvT) and holo-ovotransferrin with a degree of iron saturation between 0.5 and 15% not only increased the cell viability on the gastric and intestinal cell models with respect to the holo-OvT 100%, when tested at the same concentrations, but also showed a surprisingly better time dependent absorption of iron ions showing a physiological trend which suggests the possibility of a single oral administration in 24 hours. The mediated slow release and increased absorption of iron ions in the gastrointestinal tract without accumulation of iron ions and excluding gastric and intestinal irritability, represent a clear and unexpected advantage compared to the use of holo-OvT 100%.

According to a first embodiment, the invention provides ovotransferrins with an iron content from 1-10 ppm to 201-246 ppm, corresponding to a degree of iron saturation from 0 to 15% for use in the treatment of iron deficiency and iron deficiency anaemia.

According to the invention, either apo-ovotransferrin having iron saturation substantially equal to zero (typically less than 10 ppm of iron ions) or ovotransferrins having an iron content from 20-25 ppm to 201-246 ppm, corresponding to a degree of iron saturation from about 0.5 to 15%, preferably 15%, may be used.

According to a second embodiment, the invention provides a composition comprising as active ingredient an ovotransferrin with an iron content from 1-10 ppm to 201-246 ppm, corresponding to a degree of iron saturation from 0 to 15% in combination with pharmaceutically or alimentary acceptable ingredients.

The term "about" should be interpreted to mean±10% of the individual numerical value. For instance, 150-152 ppm accordingly corresponds to a range of 135-170 ppm and 22 ppm corresponds to 20-25 ppm. A conversion table of the iron content parameters is reported below.

| ppm of iron in Ovotransferrin | mg iron/g Ovotransferrin | % Ovotransferrin saturation | mequivalent iron ion/molecule Ovotransferrin |
|---|---|---|---|
| 1490.00 | 1.49 | 100.00 | 2.00 |
| 745.00 | 0.75 | 50.00 | 1.00 |
| 372.50 | 0.37 | 25.00 | 0.50 |
| 223.50 | 0.22 | 15.00 | 0.30 |
| 0.00 | 0.00 | 0.00 | 0.00 |

OvTs according to the invention and the formulations containing the same can be safely utilized for the treatment of iron deficiency (ID) and iron deficiency anaemia (IDA), also in case of increased physiological needs (for example in women during pregnancy, menstruations, in infant and children). Differently from the standard therapy of ID and IDA, which provides the administration of additional amount of iron in the diet in the forms of organic (e.g. ferrous fumarate, ferrous gluconate) or inorganic salts (ferrous sulphate) or iron complexes (iron polymaltose complex), the invention allows to increase in a physiological way the absorption of iron ions already present in the ingested food and therefore avoiding any potential undesirable effect due to the iron toxicity.

DETAILED DESCRIPTION

It has been found that ovotransferrins with an iron content from 1-10 ppm to 201-246 ppm, corresponding to a degree of iron saturation from 0 to 15%, (apo-ovotransferrin (apo-OvT) and holo-ovotransferrin with an iron content from 20-25 ppm to 201-246 ppm,) compared favourably with holo-OvT (100% iron saturation) in terms of cell viability, gastric and intestinal permeability and gastric and intestinal iron absorption.

The above-mentioned characteristics of the OvT having an iron content from 1-10 ppm to 201-246 ppm, corresponding to an iron saturation from 0 to 15%, are not only superior with respect to holo OvT 100% but are also equal to or superior with respect to the tested sample of bLact.

Particularly, both apo-OvT (iron saturation=0, ppm below 10 ppm) and Ovts with an iron saturation between 0.5 and 15% (from 20-25 ppm to 201-246 ppm, preferably 221-227 ppm) induce less expression of ferritin and therefore potentially less in-vivo irritability on gastric and intestinal cells and promote a more controlled iron absorption on an in vitro gastro-intestinal model with respect to 100% iron holo-OvT.

The OvTs of the invention, at a dosage from 100 to 400 mg/day, are useful for the treatment of patients with iron deficiency (ID) or Iron Deficiency anaemia (IDA) or as diet supplementation for increasing dietary iron absorption. Differently from the standard treatment of ID and IDA, consisting in the administration of an additional amount of iron to the diet in the forms of organic (e.g., ferrous fumarate, ferrous gluconate) and, inorganic salts (ferrous sulphate) or complexes with iron (like iron polymaltose complex), the invention increases in a physiological way the absorption of the iron ions already present in the ingested food, therefore avoiding any potential undesirable effect due to iron toxicity.

When ovotransferrins with a degree of iron saturation from 0 to 15% are formulated with ferrous sulphate, the maximum daily intake is from 100 to 200 mg, preferably 200 mg, of iron sulphate; when formulated with ferrous fumarate, the maximum daily intake is from 110 to 224 mg, preferably 224 mg, of ferrous fumarate; when formulated with ferrous gluconate, the maximum daily intake is from 295 mg to 590 mg, preferably 590 mg of ferrous gluconate. Ovotransferrins of the invention can be used as a nutritional ingredient/dietary ingredient in iron-fortified products such as iron food supplements/dietary supplements, iron-fortified beverages, iron-fortified mixtures for instant drinks, sport bars and protein supplements, and also in infant foods and foods for children and in fortified foods. The daily dosage can be easily derived by a skilled reader from in vitro data obtained by the gastrointestinal model utilized as disclosed by P. Artursson and J. Karlsson in Biochemical and Biophysical Research Communications Mar. 29, 1991 880-885 and in Cells, 175, (3), 1991, K-C Cheng, Cheng Li & Annette S Uss, Prediction of oral drug absorption in humans—from cultured cell lines and experimental animals, Expert Opin. Drug Metab. Toxicol. (2008) 4(5) and Shinji Yamashita, Tomoyuki Furubayashi, Makoto Kataoka, Toshiyasu Sakane, Hitoshi Sezaki, Hideaki Tokuda, Optimized conditions for prediction of intestinal drug permeability using Caco-2 cells, European Journal of Pharmaceutical Sciences 10 (2000) 195-204).

In the examples, a direct comparison with a commercially available substance utilized for iron supplementation, bovine lactoferrin, is provided. The recommended daily dose for bovine lactoferrin is well known (Scientific Opinion on bovine lactoferrin. EFSA Journal 2012; 10(5):2701. 26 pp.).

The claimed OvTs with a degree of iron saturation of 0-15% may be used alone or mixed within foods (including liquids) or formulated with foods (including food intended for infants and young children, food for special medical purposes, and total diet replacement for weight control) or formulated with other food ingredients and/or additives or formulated with other active ingredients and pharmaceutical excipients, for the preparation of solid (for example capsule, tablets, powders, bars), semi-solid (for example oral gel or oral paste) and liquid formulations (for example syrups, oral drops, oral suspensions) which can be used to supplement the diet in case of increased physiological need of iron (for example during pregnancy, during menstruations or after surgery), or for maintenance of the good iron blood level, or to treat patients with iron deficiency (ID) or iron deficiency anaemia (IDA).

Ovotransferrin of the present invention can also be administered in association with inorganic and/or organic iron compounds (for example ferrous carbonate, ferrous citrate, ferric ammonium citrate, ferrous gluconate, ferrous fumarate, ferric sodium diphosphate, ferrous lactate, ferrous sulfate, ferric diphosphate (ferric pyrophosphate), ferric saccharate, elemental iron (carbonyl+electrolytic+hydrogen reduced), ferrous bis-glycinate, ferrous L-pidolate, ferrous phosphate, ferrous ammonium phosphate, ferric sodium EDTA) up to a maximum elemental ion content equivalent of 74 mg/day (examples in Table 1).

TABLE 1

Weight composition (mg) of the claimed formulations containing OvTs alone or in association with other iron containing compounds (additives or other food ingredients or excipients not reported)

| Formulation number | Apo OvT (mg) | OvT 15% (mg) | FeSO4 (mg) | ferrous fumarate (mg) | ferrous gluconate (mg) |
|---|---|---|---|---|---|
| 1 | 100-400 | 0 | 0 | 0 | 0 |
| 2 | 0 | 100-400 | 0 | 0 | 0 |
| 3 | 100-400 | 0 | 100-200 | 0 | 0 |
| 4 | 0 | 100-400 | 100-200 | 0 | 0 |
| 5 | 100-400 | 0 | 0 | 110-224 | 0 |
| 6 | 0 | 100-400 | 0 | 110-224 | 0 |
| 7 | 100-400 | 0 | 0 | 0 | 295-590 |
| 8 | 0 | 100-400 | 0 | 0 | 295-590 |

Examples of suitable excipients for the preparation of the above-mentioned formulations include:

1. Liquid formulations (100 ml syrup): sucrose 37-38% w/w; glycerol 8-12% w/w; methyl p-hydroxybenzoate: 70-80 mg; ethyl p-hydroxybenzoate: 37-38 mg; propyl p-hydroxybenzoate: 37-38 mg; dehydroacetic acid (sodium salt): 50 mg; purified water q.b. to 100 ml.
2. Capsules: talc: 10-13 mg; magnesium stearate: 2-10 mg; silica colloidal anhydrous: 3-6 mg; maize starch: 2 mg; colloidal silicon dioxide 6 mg; gelatin: 79 mg; titanium dioxide (E 171): 1 mg.
3. Powder for oral solution: mannitol 0.8-2 g; saccharin sodium 5-20 mg; citric acid 40-90 mg; flavour 50-100 mg.

The biological tests performed with ovotransferrins with a degree of iron saturation from 0 to 15% are detailed in the following experimental part and in the annexed figures.

MATERIALS AND METHODS

Figure 1:
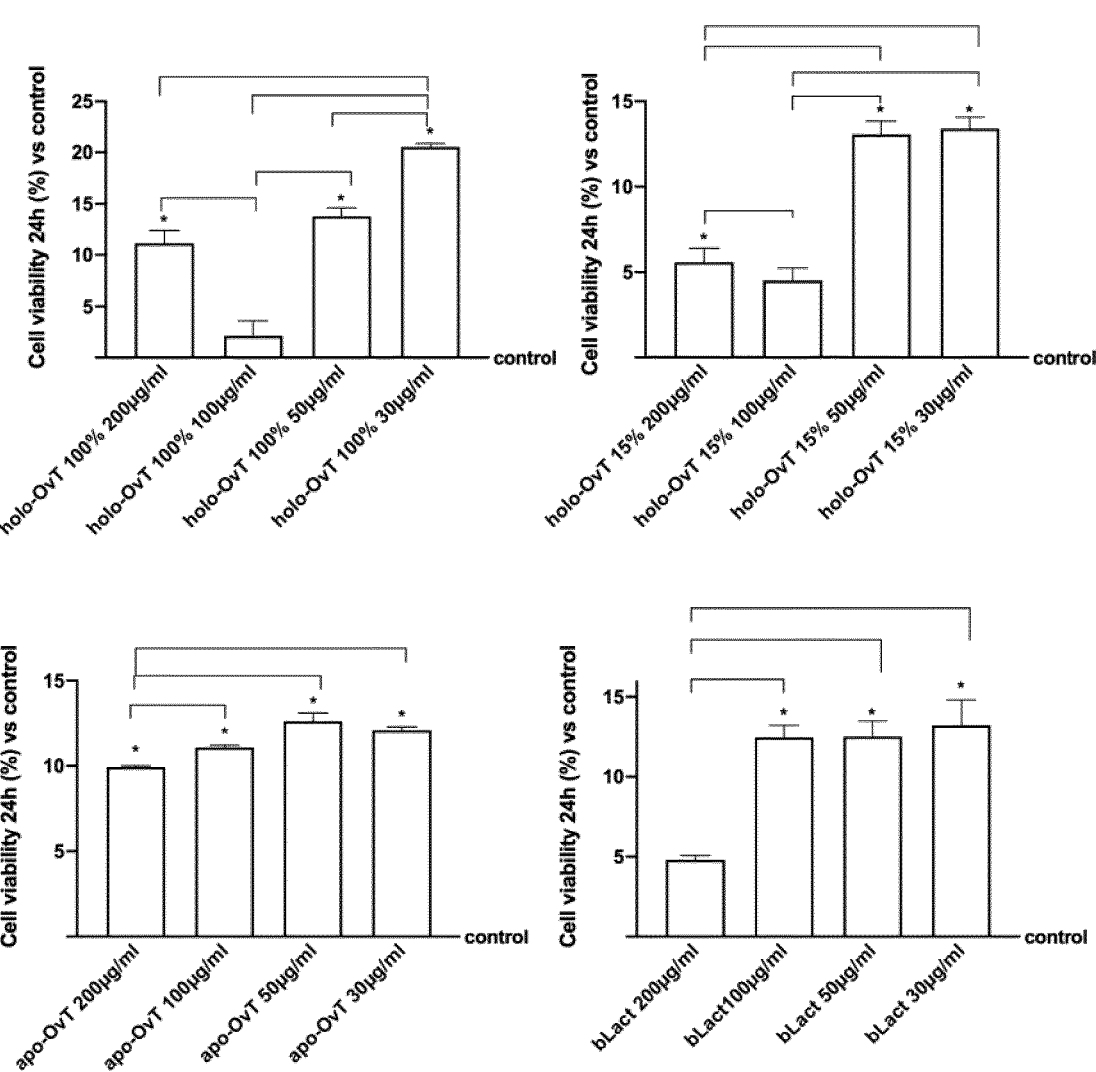
FIG. 1: Cell Viability on GTL-16 and CaCo2 treated with different concentrations and different iron saturation types of OvT. Data are expressed as +/−SD (SEM Vertical bar) compared to control of four independent experiments produced in triplicate. *$p<0.05$ vs. control; bars $p<0.05$ among different concentrations.
Figure 1:
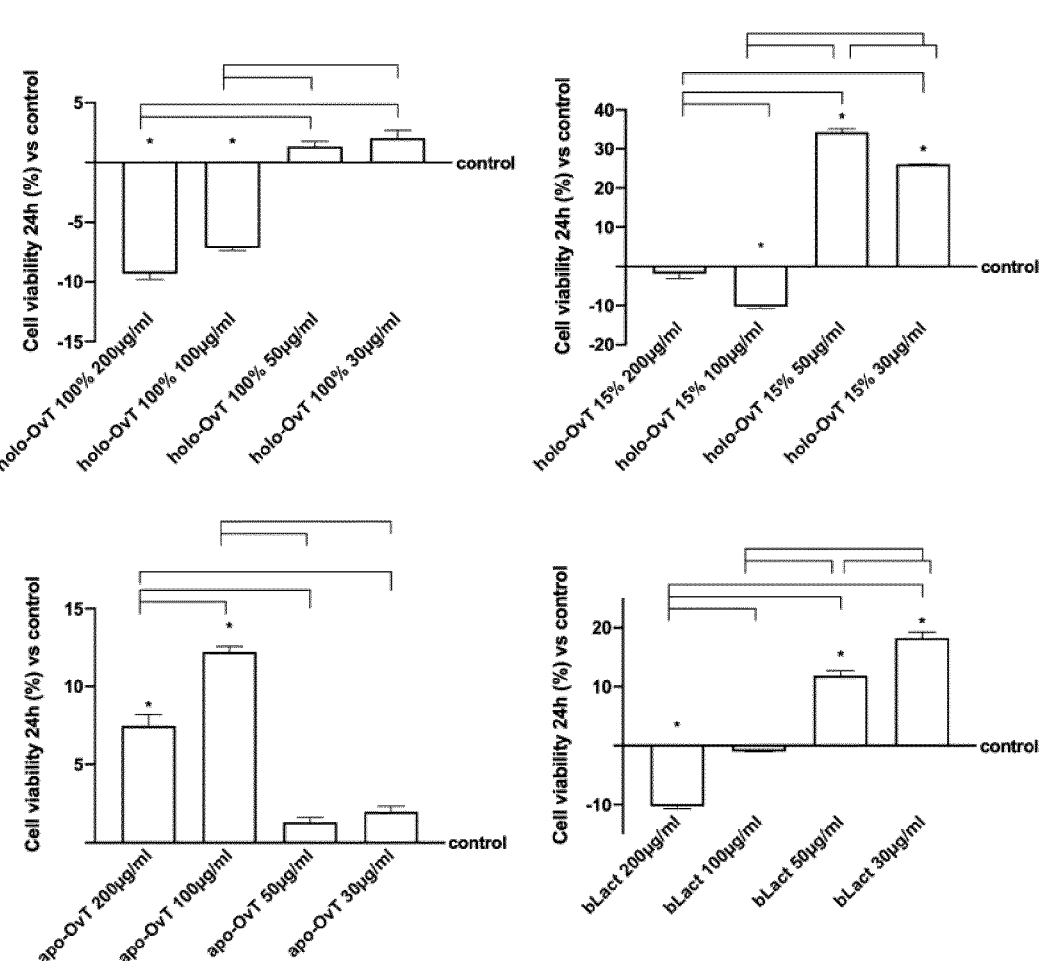

Purified ovotransferrin from hen egg white have been supplied by BIOSEUTICA BV (NL) with different degree of iron saturation: apo form (not iron-bound) and holo form (iron-bound), the latter having 2 different degrees of iron saturation: 15% and 100% saturation. bLact employed in this study was purchased from the market (Biocon (Japan) LTD) and further analyzed by ICP showing an iron content of 157 ppm, which corresponds to a 11% iron saturation.

Caco-2 cell line, supplied by the American Type Culture Collection (ATCC), was cultured in DMEM-F12 (Sigma-Aldrich, St. Louis, US) containing 10% FBS (Sigma-Aldrich), 2 mM L-glutamine (Sigma-Aldrich), and 1% penicillin-streptomycin (Sigma-Aldrich) at 37° C. in an incubator at 5% $CO_2$ (Christides, T et al. In-vitro assessment of iron availability from commercial Young Child Formulae supplemented with prebiotics. Eur. J. Nutr. 2016, 9, 1-10). Caco-2 cells were plated at $1×10^4$ cells in 96-well plates to study cell viability via the MTT test and to analyze the intracellular pathways through western blot analysis, cells were plated on 60-mm culture dishes until confluence. For absorption study, cells were plated $2×10^4$ cells on 6.5 mm Transwell® with 0.4 μm pore polycarbonate membrane insert (Sigma-Aldrich) in a 24-well plate and cells were maintained in complete medium, changed every other day, first basolaterally and then apically for 21 days before the stimulations.

GTL-16 cell line is a clonal line derived from a poorly differentiated gastric carcinoma cell line (Giordano S et al. p145, a protein with associated tyrosine kinase activity in a human gastric carcinoma cell line. Mol Cell Biol. 1988; 8:3510-7) and is widely used as a model of gastric epithelial cells. This cell line was donated by the Laboratory of Histology of the University of Eastern Piedmont (Novara, Italy). Cells were cultured in Dulbecco's Modified Eagle Medium (DMEM) supplemented with 10% fetal bovine serum (FBS), 1% penicillin-streptomycin in incubator at 37° C., 5% $CO_2$. The cells for the experiments were plated in different ways: to study cell viability (MTT test) and to analyze the intracellular pathways through Western blot analysis the cells were plated on 60 mm dishes until confluence. Before stimulation, the cells were maintained in DMEM without red phenol and FBS and supplemented with 1% penicillin/streptomycin, 2 mM L-glutamine and 1 mM sodium pyruvate in incubator at 37° C., 5% $CO_2$, and 95% humidity for 18 h. Then the cells were treated with different agents in DMEM without red phenol and supplemented with 0.5% FBS, 1% penicillin/streptomycin, 2 mM L-glutamine and 1 mM sodium pyruvate. GTL-16 cells were plated $2×104$ onto 6.5 mm translucent polyethylene terephthalate (PET) Transwell® insert 0.4 μm in a 24 well-plate to study absorption and were maintained in complete medium, changed every other day, first basolaterally and then apically for 21 days before the stimulations.

Cell Proliferation Kit I (MTT). MTT dye (Sigma-Aldrich) was used to determine cell viability. After stimulation, cells were incubated with 1% MTT dye for 2 h at 37° C. in incubator as described in literature (Natoli M et al. *Cell growing density affects the structural and functional properties of Caco-2 differentiated monolayer*. J Cell Physiol. 2011 June; 226(6):1531-43). The purple formazan crystals (3-[4,5-dimethylthiazol-2-yl]-2,5-diphenyl tetrazolium bromide) were dissolved in DMSO. Cell viability was determined by measuring the absorbance through a UV spectrometer (VICTOR X3 Multilabel Plate Reader) at 570 nm with correction at 690 nm, and cell viability calculated by comparing results to control cells (100% viable).

Gastric model. A first model has been setup to mimic a gastric system. An in-vitro gastric barrier model has been created using gastric epithelial cells GTL-16 subclone derived from MKN-45 cells. This model employs human gastric epithelial cells, derived from squamous adenocarcinoma that maintains a wild type phenotype, thus preserving both the kinase activities and the phenotypic expression unchanged. The employed model has been validated in literature (Fernandes I et al. A new approach on the gastric absorption of anthocyanins. Food Funct. 2012 May; 3(5): 508-16; Uberti F et al. *Iron Absorption from Three Commercially Available Supplements in Gastrointestinal Cell Lines*. Nutrients. 2017 Sep. 13; 9(9).). This model allows to measure the permeability and the integrity of the gastric barrier. At the end of 21 days, it has been possible to start the treatment to evaluate the passage to the underlying layer in terms of cell viability (in order to exclude any toxicity), free radical production (to exclude adverse effects), and concentration of iron using a special kit (Iron Assay). This data is relevant to determine the proportion of the OvT products (100% and 15% holo-OvT over the limit of efficacy comparable to 11% holo-bLact from the market; apo-OvT) that can reach the intestine or be readily available, compared to commercial product. The treatment has been evaluated for 4 hours (maximum absorption time of the molecules) and on-time points as follows: 1 h-2 h-3 h-4 h. The same conditions have been reproduced in presence of iron 3+ to define the mechanism under conditions of food supplementation. In addition, the iron transport mechanism has been analyzed by Western blot [2,3] for ferritin, ferroportin, DMT-1.

Intestinal model. A second model has been set up for the bioavailability study after the transition from the intestinal system. For this reason, an in-vitro intestinal barrier model has been created, according to the model below reported, using CaCo-2 cells. After 21 days of growth, cells were ready and it was possible to start treatments, evaluating the transition to the underlying layer in terms of cell viability or layer integrity (to exclude any toxicity), free radical production (to exclude adverse effects) and iron concentration physiologically present by means of a special kit (Iron assay). These tests have been maintained at the same experimental conditions and treatments of the first model (i.e. mimic a gastric system). The treatment has been evaluated over a period of 6 h (maximum time of absorption of the molecules), with on-time points of 1 h-2 h-3 h-4 h-5 h-6 h. The same conditions have been reproduced in presence of iron 3+ to identify the mechanism in conditions of food supplementation.

The iron transport mechanism has also been analyzed for ferritin, ferroportin, DMT-1.

3D gastro-intestinal model: To evaluate if the two models, gastric and intestinal, separately observed, are really able to promote the increase of plasma iron, a further three-dimensional (3D) model has been used, that allows to put the two cell populations (gastric and intestinal) in direct communication, mimicking what happens in a complex organism (gastro-intestinal model). The 3D model Vitvo® has been used for this experiment. Two fundamental parameters have been analyzed using this model: the concentration of OvT and iron Caco-2 Permeability assay. After 21 days, two different concentrations of OvT and bLact were added to culture medium under different pH conditions, as reported in literature (Natoli M et al. A. *Cell growing density affects the structural and functional properties of Caco-2 differentiated monolayer*. J Cell Physiol. 2011 June; 226(6):1531-43; Uberti F et al. *Iron Absorptionfrom Three Commercially Available Supplements in Gastrointestinal Cell Lines*. Nutrients. 2017 Sep. 13; 9(9):1008). During treatments, the cells were maintained in incubator at 37° C., 5% $CO_2$, and, at the end of stimulations, the iron quantity and OvT/bLact concentration were measured by specific kit.

GTL-16 Permeability assay. After 7 days, to study the effects on absorption of apical-to-basolateral pH gradients, the medium was changed on both the apical and basolateral sides adding HCl to the medium to obtain pH 3 at the apical side for 60 min, as reported in the literature [8,7]. At the defined time scheduled, the treatments were performed in the same conditions and manner as previously described, and then iron quantity and OvT/bLact concentration were detected with the kit.

bLact Determination. The concentration of bLact which crossed through gastric and intestinal barriers was measured according the method below described. At the end of stimulations, the basolateral volume was analyzed through a UV spectrometer (VICTOR X4, multilabel plate reader) at 320 nm, and the absorbance related to the standard curve was obtained. The results were expressed as means±SD (%) of absorption, normalized to the control.

OvT Determination. The concentration of OvT which crossed through gastric and intestinal barriers was measured according the method below summarized. Briefly, at the end of stimulations, the basolateral volume was analyzed through a UV spectrometer (VICTOR X4, multilabel plate reader) at 450 nm, and the absorbance related to the standard curve was obtained. The results were expressed as means±SD of absorption compared to the control.

Lactoferrin Ovotransferrin Quantification Assay. The Human Transferrin ELISA kit is designed to measure the amount of the target bound between a matched antibody pair following the manufacturer's instructions. A target-specific antibody has been pre-coated in the wells of the supplied microplate. Samples are added into these wells and bind to the immobilized (capture) antibody. The sandwich is formed by the addition of the second (detector) antibody, in particular a substrate solution is added that reacts with the enzyme-antibody-target complex to produce measurable signal. The intensity of this signal is directly proportional to the concentration of target present in the original specimen. Briefly, 100 μL of diluted samples were incubated overnight at 4° C., washed 4 times with 1× Wash Buffer and then 100 μL of biotin conjugate were added to each well and incubated for 1 hour at room temperature with gentle shaking. Then the wells were washed 4 times and 100 μL of Streptavidin-HRP and 100 μL of TMB Substrate were added. Finally, the plate was incubated for 30 minutes at room temperature under dark with gentle shaking and stopped with 50 μL of Stop Solution. The absorbance was measured by spectrometer at 450 nm (VICTOR X4, multilabel plate reader).

Iron Quantification Assay. Iron Assay Kit (Sigma-Aldrich) which measures ferrous iron ($Fe^{2+}$), ferric iron ($Fe^{3+}$), and total iron (total iron-ferrous iron) in samples was used on astrocytes following the manufacturer's instructions. The absorbance at 593 nm was measured by a spectrometer (VICTOR X4, multilabel plate reader). Ferric iron concentrations are equal to the total iron (sample plus iron reducer)-$Fe^{2+}$ (sample plus assay buffer). The results were expressed as means±SD (%) of absorption, normalized to the control.

Western Blot for ferritin, ferroportin, DMT-1. Caco-2 and GTL-16 cells were washed and then lysed in ice with Complete™ Tablet buffer (Roche, Basel, Switzerland) supplemented with 2 mM sodium orthovanadate ($Na_3VO_4$), and 1 mM phenylmethanesulfonylfluoride (PMSF; Sigma-Aldrich), 1:50 mix phosphatase inhibitor cocktail (Sigma-Aldrich), and 1:200 mix Phosphatase Inhibitor Cocktail. A quantity of 35 μg of protein from each lysate was loaded on 15 or 5% SDS-PAGE gels and transferred to polyvinylidene fluoride membranes (PVDF, GE Healthcare Europe GmbH, Milan, Italy). These were incubated overnight at 4° C. with specific primary antibodies: anti-ferritin (1:1000, Santa-Cruz), anti-ferroportin-1 (1:2000, Santa-Cruz), anti-DMT-1 (1:400, Santa-Cruz). Protein expression was normalized and verified through β-actin detection (1:5000; Sigma, Milan, Italy) and expressed as mean SD (% vs control).

Statistical analysis. For each protocol, at least five independent experiments were performed and the results are expressed as means SD of independent experiments performed on four technical replicates. One-way ANOVA followed by Bonferroni post hoc tests were used for statistical analysis, and pairwise differences compared by Mann-Whitney U tests. p-value<0.05 were considered statistically significant.

Experimental Section

Preparation of Ovotransferrin 15% Iron Saturated (Holo OvT 15%)

Load in a glass line reactor water (5 liters) and under stirring at room temperature Apo-Ovotransferrin (680 g; 8 mmol) and maintain the mixture under stirring at room temperature for 3 hours. Sodium bicarbonate (0.21 g) is the added to the reaction mixture, under vigorous stirring, to a final stable pH value of 8.54 then, after 30', $FeCl_3 \cdot 6H_2O$ (0.59 g; 2.2 mmol) was added and the final pH value maintained to 8,8±0,2 by addiction of a 10% sodium carbonate aqueous solution. After 15' under stirring at room temperature, Celite® (10.98 g) was added and the obtained mixture filtered under pressure on a 6 Filtrox AF6 panel model. The filtrate is then freeze dried to afford 580 g of Holo OvT 15%.

The ICP analyses of this product confirmed a final iron content of 210 ppm. The iron saturation of the obtained product was also confirmed to be 15% by a spectrophotometric titration at 465 nm against the apo OvT form saturated with and excess of $FeCl_3$-$6H_2O$ in a 20 mM citrate/bicarbonate buffer at pH 9,0.

Preparation of Ovotransferrin 100% Iron Saturated (Holo OvT 100%)

The above-described procedure for the preparation of holo Ovt 15% was applied, with some modifications, also for the preparation of holo OvT 100% using 7 mol of $FeCl_3 \cdot 6H_2O$ for 1 mol of apo Ovt (relative ratio between OvT/iron 3+=1/7 instead of 1/0.28 utilized for the preparation of holo OvT 15%). In this process before the freeze drier treatment the mixture was ultrafiltered to remove the excess of iron salts on a 50 KDalton membrane and then filtered on a 3 μm filter. The ICP analyses of this product confirmed a final iron content of 1400 ppm.

Dose-Response Study of Cell Viability on GTL-16 and Caco2 Cells

Different concentrations of OvT (apo and holo forms with different degree of iron saturation) and bLact have been tested for 24 h, and from this dose-response study, it was possible to identify the concentrations influencing the viability of GTL-16 and CaCo2 cells prior to start the experiments. Since the test products are different and could affect the cell viability, the MTT test was performed on gastric and intestinal cells. The selected concentrations for all the test products have been: 200 μg/ml, 100 μg/ml, 50 μg/ml and 30 μg/ml. All the OvT samples tested have shown to have a positive effect on cell viability, at least comparable to bLact (FIG. 1).

These data confirmed that the two lower concentrations 50 μg/ml and 30 μg/ml of the three OvT tested have an effect comparable to bLact and no cytotoxicity on the gastric and intestinal cells, even though holo-OvT 15% saturated and apo-OvT has shown to be better in terms of mitochondrial metabolic well-being.

Time-Dependent Study on GTL-16 and Caco2 Cell Line

Figure 2:
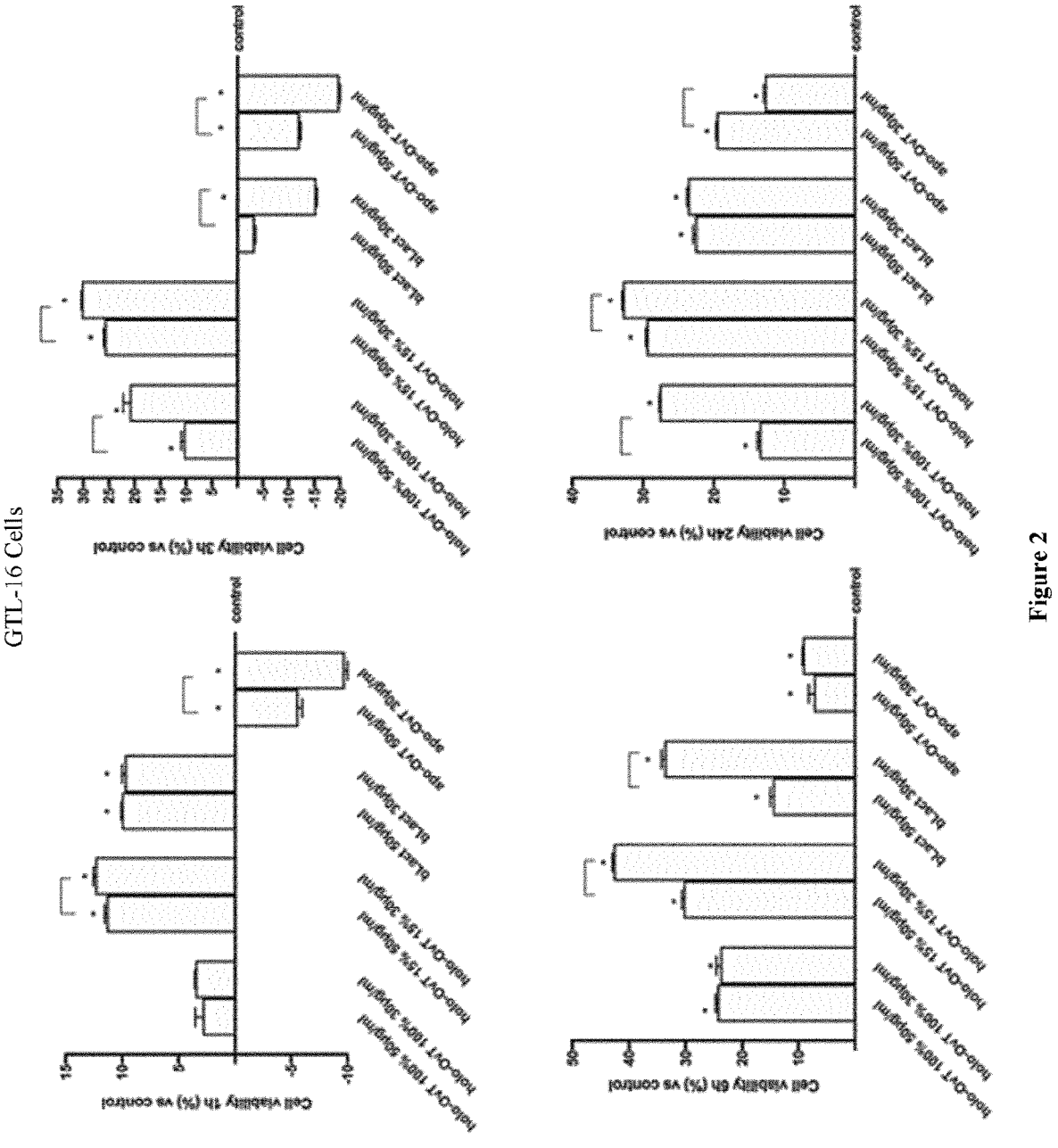
FIG. 2: Cell Viability on GTL-16 and Caco2 cells treated with 50 μg/mL and 30 μg/mL for 1, 3, 6 and 24 hours. Data are expressed as +/−SD (%) (SEM Vertical bar) compared to control of four independent experiments produced in triplicate. *$p<0.05$ vs. control; the bars are $p<0.05$ vs. the two concentrations tested.
Figure 2:
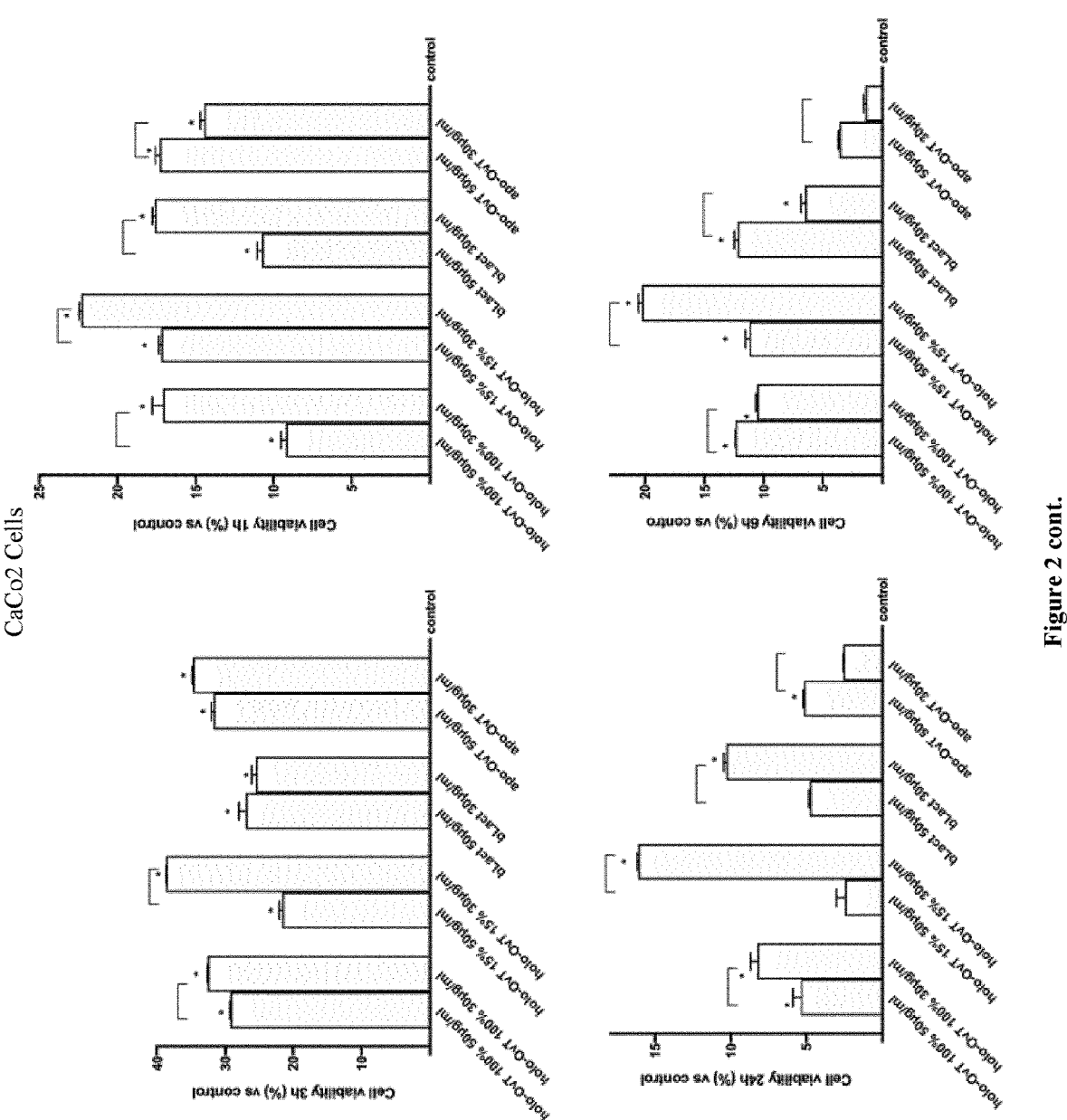

On the basis of these tests 30 μg/ml and 50 μg/ml concentrations have been selected for all subsequent experiments: GTL-16 and CaCo2 cells have been stimulated with the 3 different iron saturation OvT at the above selected concentration (i.e. 50 μg/mL and 30 μg/mL) for 1, 3, 6 and 24 hours. At the end of the stimulations, an MTT test was performed to evaluate cell viability. As shown in FIG. 2, a time dependent effect has been revealed on GTL-16 with a maximum effect for the 2 holo-OvT 100% and 15% saturated at 6 hours (p<0,05). Holo-OvT 15% saturated has shown to be the best compared to control throughout the entire analysis process at different timeframe, as well as when compared to holo-OvT 100% saturated (p>0,05).

In particular, for Holo-OvT 15% iron saturated the effects are maintained also at 24 hours indicating a slow-release mechanism with a better physiologic profile respect to holo-OvT 100%.

Regarding the Caco2 cell, a time-dependent effect has also been observed which has reached an apex at 3 h, that was preserved at 6 h, and tended to decrease towards 24 h.

These results obtained in both cell types, have confirmed that OvT has a time-dependent effect and have suggested that holo-OvT 15% saturated at concentration of 30 μg/mL could be the best option compared to control (p<0,05) and also compared to the bLact tested. Furthermore, based on the results, one dosage in 24 h in humans can be assumed.

Time Dependent Permeability of Gastro-Intestinal Barrier after Stimulation with Ovotransferrin In order to study the biological functions of OvT, some experiments were performed to evaluate the OvT absorption on GTL-16 cells, Caco-2 cells and in a 3D model mimic the gastro-intestinal barrier.

Figure 3:
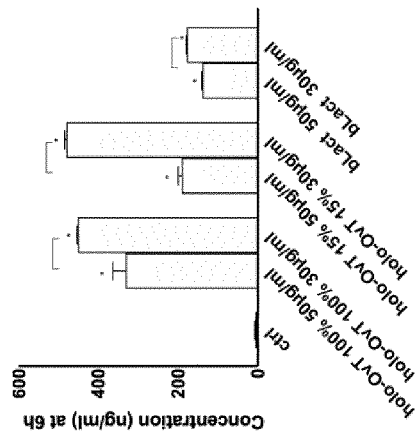
FIG. 3: Total absorption measured at the basolateral level on Transwell® during time (1, 3 and 6 hours). GTL-16 cells treated with 50 μg/mL and 30 μg/mL of different holo-OvT and bLact. Data are expressed as +/−SD (%) compared to control of four independent experiments produced in triplicate. *$p<0.05$ vs. control; the bars are $p<0.05$ vs. the two concentrations tested.
Figure 3:
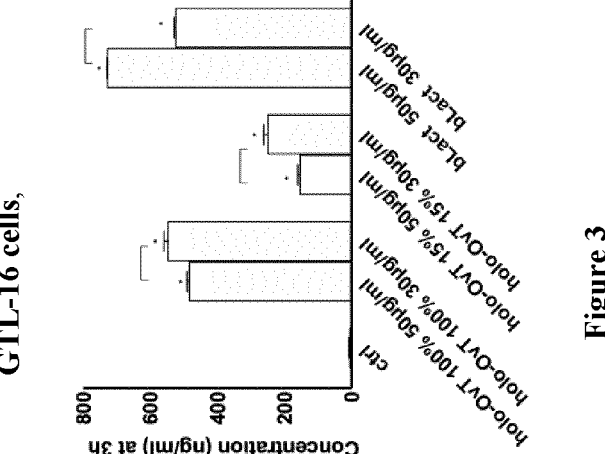
Figure 3:
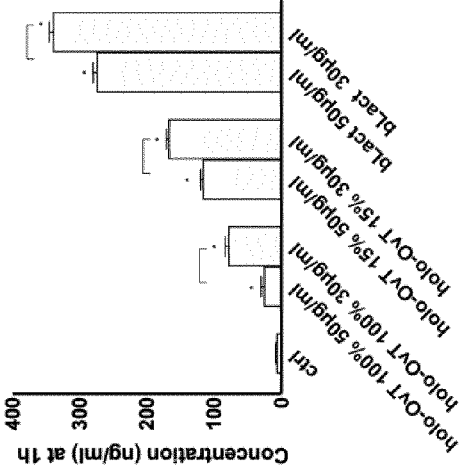

As shown in FIG. 3, the analysis of the basolateral environment of the gastric compartment (GTL-16 cell) has shown a slow but constant gastric absorption over time (1, 3 and 6 hours), confirming again a "slow-release effect". Overall, holo-OvT 15% saturated has been confirmed as the best iron saturation level, compared to control (p<0,05), as well as compared to the tested bLact (p<0,05) along the timeframe of treatment (FIG. 3). Overall, the data have shown that holo-OvT 15% saturated at a concentration of 30 μg/mL, is comparable to the higher concentration 50 μg/mL of bLact test product.

Figure 4:
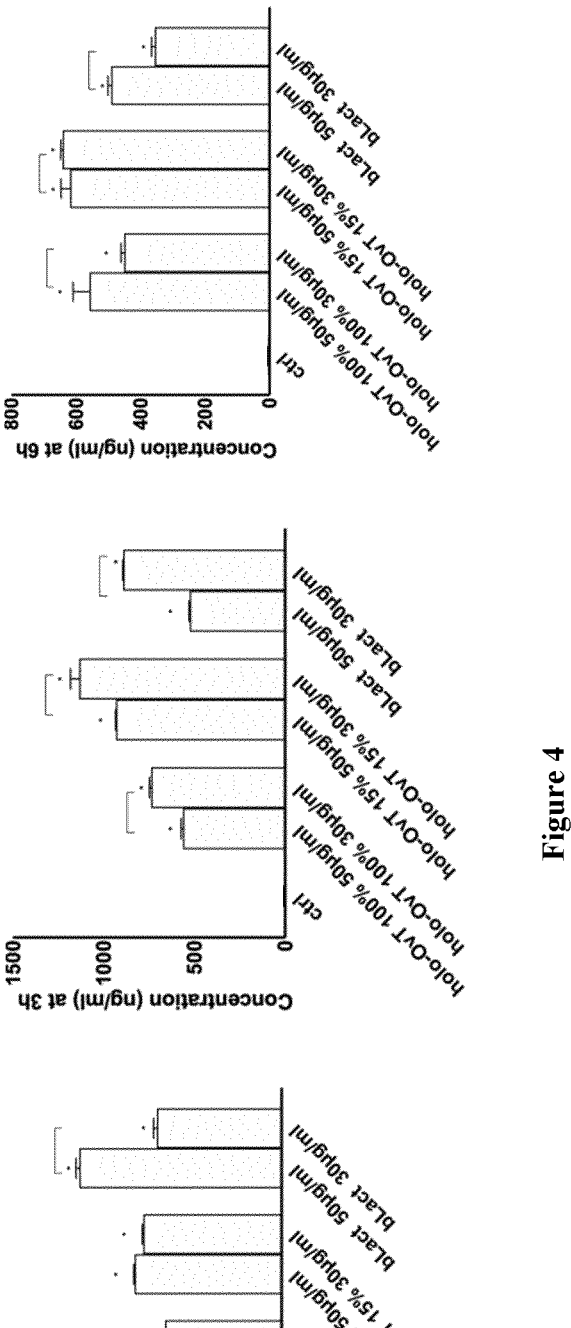
FIG. 4: Total OvT absorption measured at the basolateral level on Transwell® over time (1, 3 and 6 hours). Caco2 cell line is treated with 50 μg/mL and 30 μg/mL of different OvT and bLact. Data are expressed as +/−SD (%) compared to control of four independent experiments produced in triplicate. *$p<0.05$ vs. control; the bars are $p<0.05$ vs. the two concentrations tested.

The same quantification was performed at the basolateral level of intestinal barrier model (CaCo2 cell). In FIG. 4 the quantification analysis for same timeframe of stimulation and same concentrations is reported. The data have demonstrated how intestinal adsorption has a physiological trend with maximum effect at 3 hours, which tends to reduce over the time. Here also, in the intestinal compartment, the data have demonstrated that holo-OvT 15% saturated at concentration of 30 μg/ml was the best concentration compared to control and to 50 μg/ml (p<0,05), during all time of stimulation. In particular holo-OvT 15% saturated 30 μg/mL is comparable to the higher concentration 50 μg/mL of bLact test product.

Figure 5:
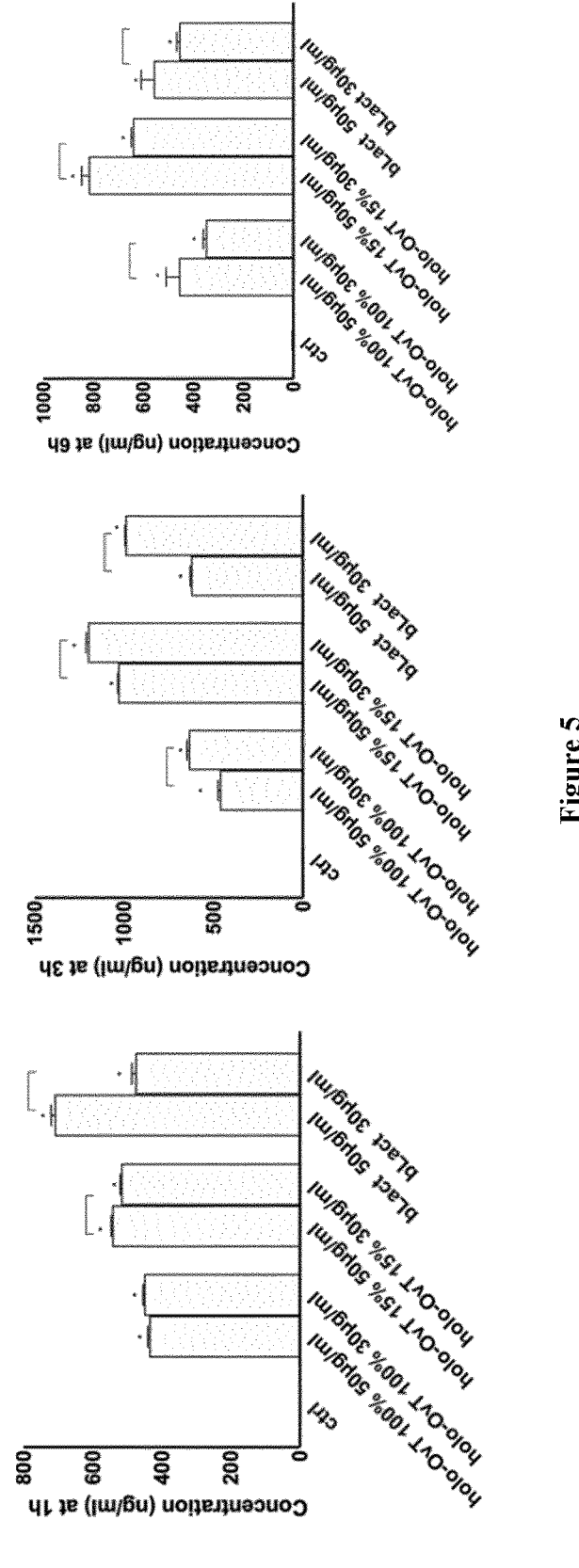
FIG. 5: Total OvT absorption measured at the basolateral level on Transwell® during time (1, 3 and 6 hours). Gastrointestinal barrier model is treated with 50 μg/mL and 30 μg/mL of different OvT. Data are expressed as +/−SD (%) compared to control of four independent experiments produced in triplicate. *$p<0.05$ vs. control; horizontal bars are $p<0.05$ vs. the two concentrations tested.

Three-Dimensional (3D) In-Vitro Model Mimickin In Vivo Complexity of the Gastro-Intestinal Barrier In order to collect more data on the compounds under investigation, respect the two experimental models (gastric and intestinal) till now used separately, we utilized a more integrated gastro-intestinal model able to replicate in vitro the complexity of the gastro intestinal barrier. For this purpose, a three-dimensional (3D) validated in-vitro model mimicking in vivo complexity of the gastro-intestinal barrier was used. An intestinal barrier was recreated in-vitro and stimulated with the basolateral part previously collected from the gastric barrier; subsequently, the basolateral part was collected and analyzed with special kits to evaluate the quantity of Ovt and bLact passed through the barrier. This model puts the two cell populations in direct communication, as in a living organism. In this context, 50 μg/ml and 30 μg/ml of holo-OvT 100% and 15% saturated have been tested at the same timeframe previously used (1, 3 and 6 hours). The data obtained by this study (FIG. 5) confirmed that the gastro-intestinal adsorption has a physiological trend. In particular, it was observed that the predigested product (from GTL-16 cells) is absorbed with a kinetic having a maximum effect at 3 h with a slow reduction at 6 h that does not end, indicating a kind of "slow absorption" which can suggest an in vivo single administration in 24 h. In this test, the best performing and bioavailable concentration was 30 μg/ml for holo-OvT 15% saturated compared to control (p<0,05) giving a further confirmation that this holo-Ovt 15% saturated is more bioavailable compared to bLact tested products (p<0,05) and comparable to higher 50 μg/mL concentration of bLact tested product. These results demonstrated not only that holo-OvT 15% saturated 30 μg/ml is more bioavailable with respect to the tested holo-OvT 100% saturated and even compared to bLact (which is fast absorbed but seems to be less bioavailable).

Figure 6:
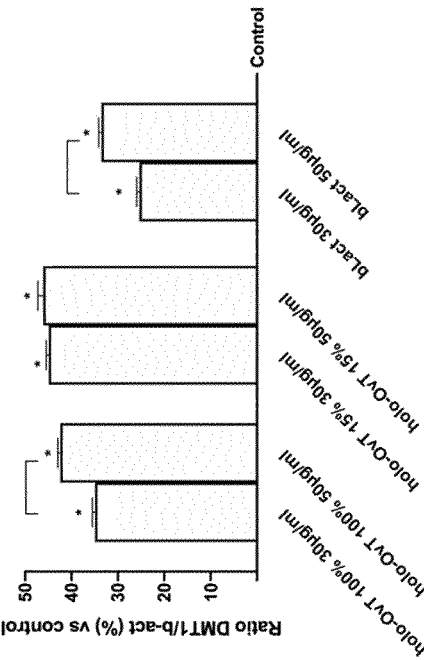
FIG. 6: Densitometric analysis of DMT-1 on GTL-16 (A) and Caco2 (B) treated with 50 μg/mL and 30 μg/mL of different OvT and bLact. The results were obtained with normalization on β-act and control, and are expressed as +/−SD (%) compared to control of four independent experiments produced in triplicate. *$p<0.05$ vs. control; the horizontal bars are $p<0.05$ vs. the two concentrations tested.
Figure 6:
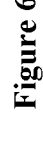
Figure 6:
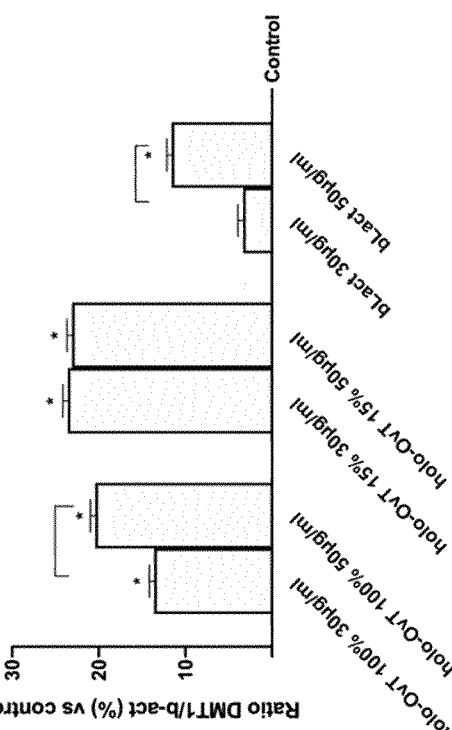

Analysis of Molecular Pathways Involved by Ovotransferrin: Evaluation on DMT-1, Ferritin and Ferroportin Expression To better define the involved mechanisms, different markers such as transferrin, ferritin, and DMT-1 have been evaluated by Western blot. DMT-1 (divalent metal transporter 1) is a very important transporter of bivalent metals, with a fundamental role in transporting ferrous ions, its effects has been analyzed by stimulating the 3D gastrointestinal barrier models with 50 μg/ml and 30 μg/ml of holo-OvT 100% saturated and 15% saturated. As shown in FIG. 6, the effects on DMT-1 expression on 3D gastrointestinal barrier model showed a greater effect with holo-OvT 15% saturated, and more in details the concentration of 30 μg/ml had a better expression compared to control and to the concentration of 50 μg/ml of bLact tested product (p<0,05). In particular, DMT-1 was expressed in both models demonstrating that OvT has the same mechanism of iron transport as bLact. Holo-OvT 15% saturated at 30 μg/ml showed a higher expression of DMT-1 also with respect to the higher concentration of 50 µg/ml of the tested bLact and also respect to OvT 100% saturated.

Figure 7:
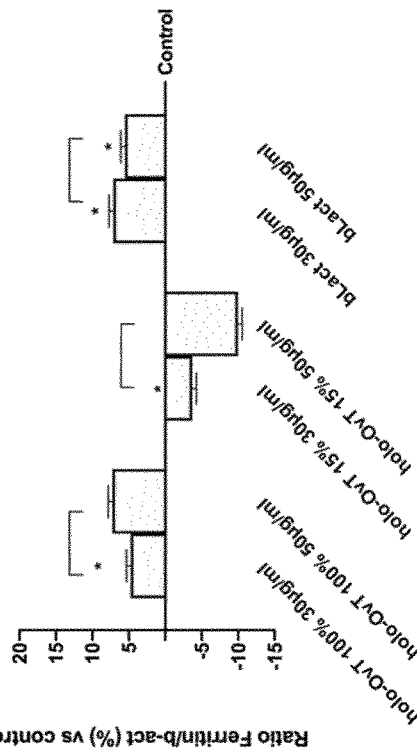
FIG. 7: Densitometric analysis of Ferritin on GTL-16 (A) and Caco2 (B) treated with 50 μg/mL and 30 μg/mL of different OvT. The results were obtained with normalization on β-act and control, and are expressed as +/−SD (%) compared to control of four independent experiments produced in triplicate. *$p<0.05$ vs. control; the horizontal bars are $p<0.05$ vs. the two concentrations tested.
Figure 7:
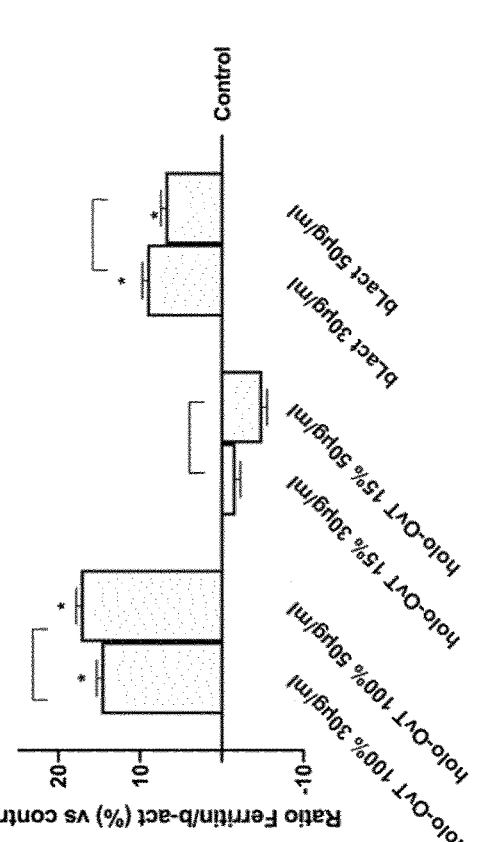

With the aim to better understand the biochemistry of the molecules under investigation on the iron metabolism we evaluate the effects on the different iron transport chains particularly of the transmembrane protein ferroportin and of the intracellular protein ferritin responsible respectively for extruding iron ions from a cell and for sequestering the iron ions in a non-toxic form inside the cells. Particularly the ferritin expression has an important role in iron homeostasis acting a reservoir of iron in the organism. The obtained data (FIG. 7) confirmed that, in both gastric and intestinal in-vitro models, after 24 h treatment with OvT and bLact, the expression of ferritin (p<0.05 vs control) was similar. The obtained results exclude iron accumulation for all products thus also excluding intestinal irritability, anyway holo-OvT 15% saturated at the concentration of 30 µg/ml seems to induce less ferritin expression respect to OvT 100% saturated and to bLact.

Figure 8:
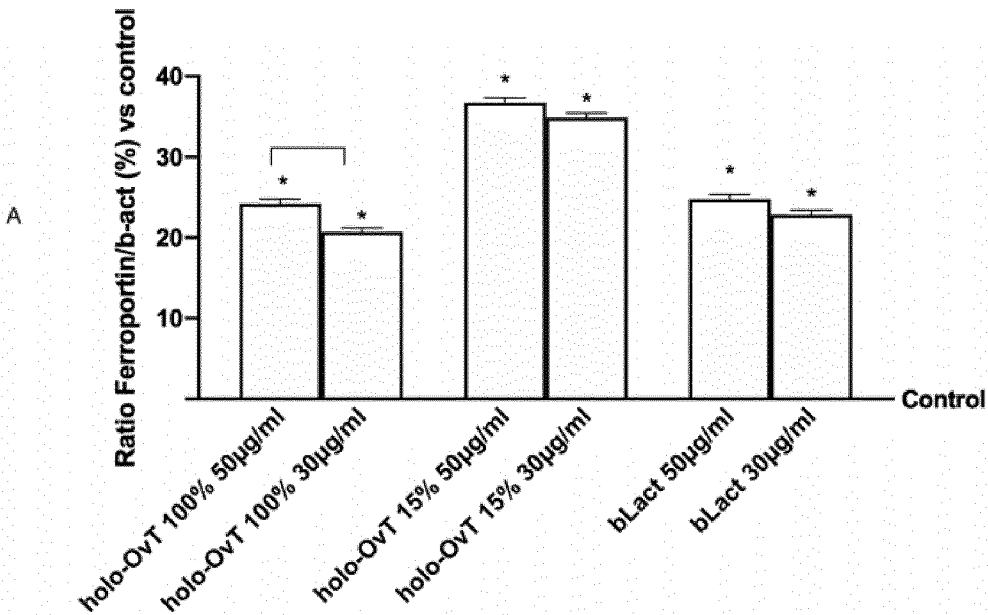
FIG. 8: Densitometric analysis of Ferroportin on GTL-16 (A) and Caco2 (B) treated with 50 μg/mL and 30 μg/mL of different OvT. The results were obtained with normalization on β-act and control, and are expressed as +/−SD (%) compared to control of four independent experiments produced in triplicate. *$p<0.05$ vs. control; the horizontal bars are $p<0.05$ vs. the two concentrations tested.
Figure 8:
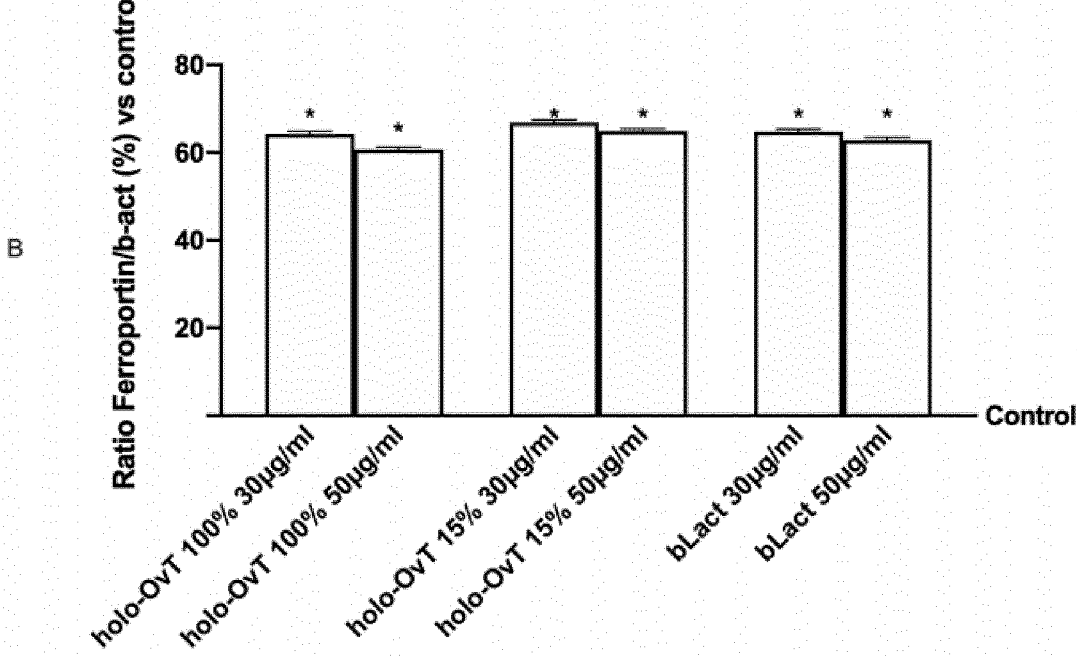

Finally, we have analyzed the expression of ferroportin: after 24 h of treatment, as shown in FIG. 8, Ferroportin expression increased all over the stimulation time (p<0.05 vs control), working as an active extrusion mechanism. These results supported the hypothesis of the absence of accumulation also in vivo. Again, in this experiments holo-OvT 15% saturated 30 µg/ml appeared to be superior to the control (p<0.05) and comparable to the highest concentration of 50 µg/ml of the tested bLact. Particularly, holo-OvT 15% saturated 30 µg/ml seems stimulate better the ferroportin expression respect to the other compounds under evaluation.

All these experiments confirmed that holo-OvT 15% iron saturated is able to exert its positive effects on the iron metabolism, and particularly on the main proteins involved in the transport and storage of iron ions in the cells, in a better way compared to the tested Holo-OvT 100% saturated and to bLact.

Dose-Response Study of Cell Viability on GTL-16 and Caco2 Cells after Pretreatment with Fe3+

Figure 9:
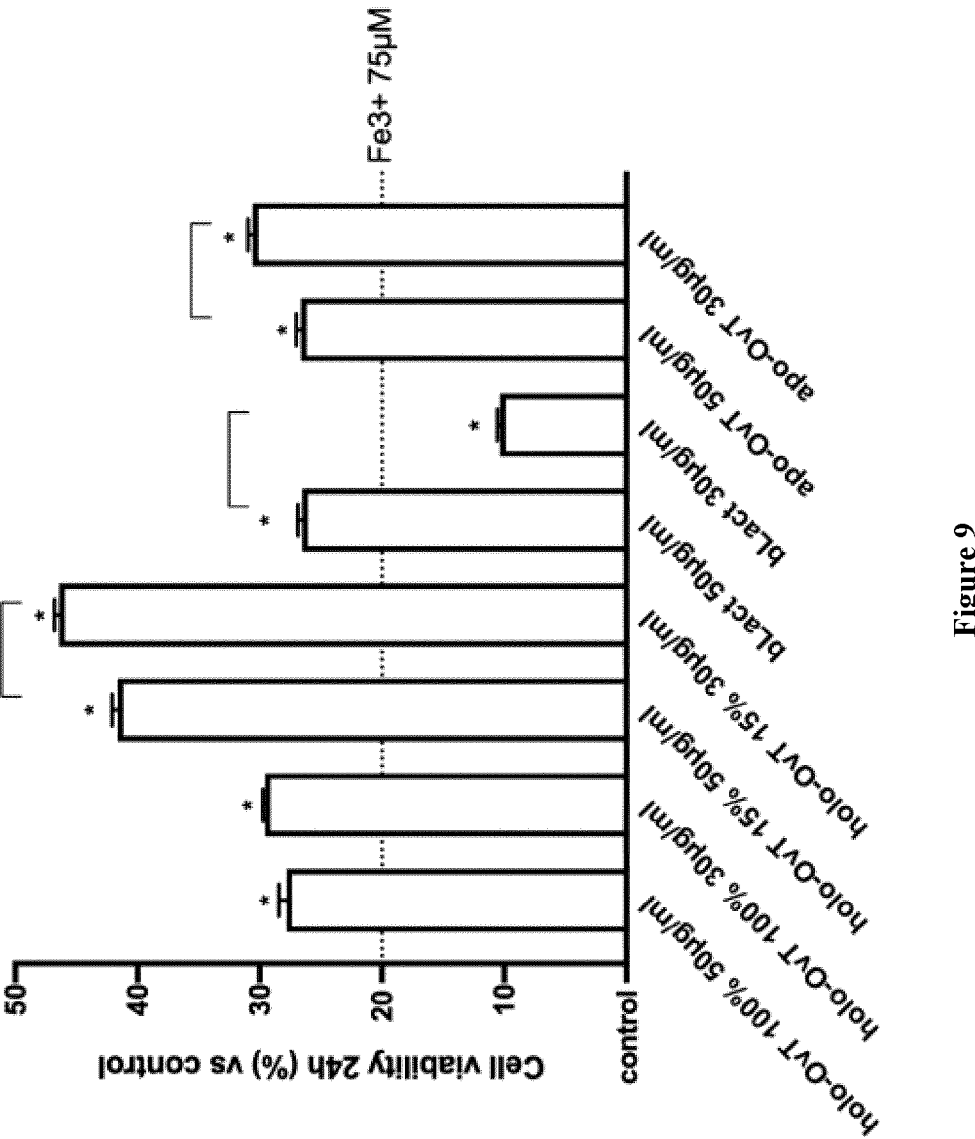
FIG. 9: Cell Viability on GTL-16 after treatment with $Fe^{3+}$. Data are expressed as +/−SD (%) compared to control of four independent experiments produced in triplicate. *$p<0.05$ vs. control; the horizontal bars are $p<0.05$ vs. the two concentrations tested.
Figure 10:
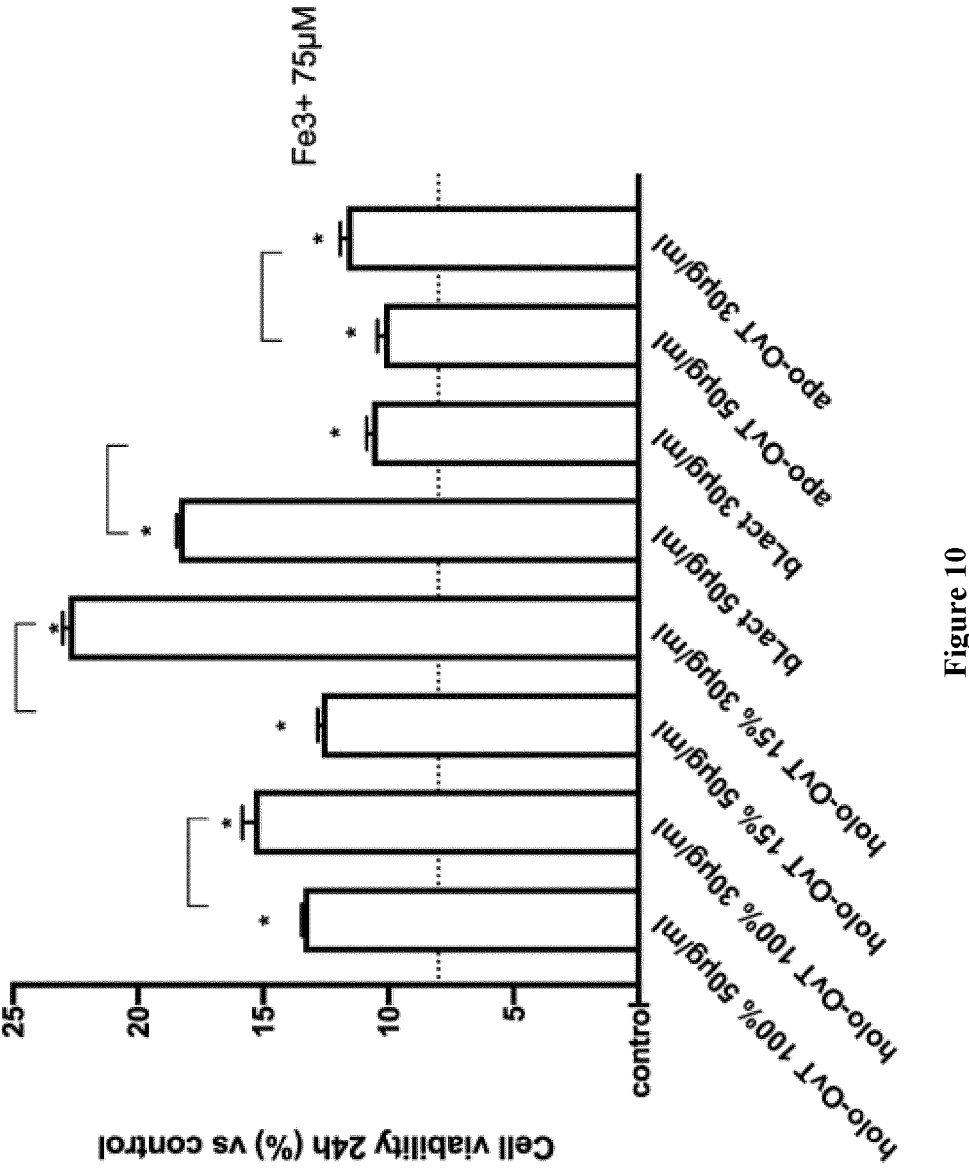
FIG. 10: Cell Viability on Caco2 after treatment with $Fe^{3+}$. Data are expressed as +/−SD (%) compared to control of four independent experiments produced in triplicate. *$p<0.05$ vs. control; the horizontal bars are $p<0.05$ vs. the two concentrations tested.

For this study only the 2 best performing concentrations of OvT and bLact, 50 µg/ml and 30 µg/ml, have been tested. Using GTL-16 cells as an in-vitro gastric model, firstly the cells have been treated with Fe3+ (final concentration 75 µM) for 24 h, then followed by the treatment with OvT and bLact for 24 h. The obtained results show (FIG. 9) that even in presence of iron, the cell viability has increased in such a way that proves the safety of the selected dosages as well as their efficacy (p<0.05 vs control). Again, in this study, holo-OvT 15% iron saturated has increased the cell viability better than holo-OvT 100% saturated and also respect to bLact. Also apo-OvT has shown to better increase the cell viability even at lower concentration. Using Caco-2 cells as an in-vitro intestinal model, the cells have been treated with Fe³⁺+(final concentration 75 µM) for 24 h then treated with OvT and bLact for 24 h. Holo-OvT 100% saturated and 15% saturated showed better results on cell viability in presence of iron (pre-treatment) compared to the tested bLact and better results compared to control (p<0.05 vs control). Overall, holo-OvT 15% iron saturated showed again better results on cell viability also with respect to holo-OvT 100% (FIG. 10).

Figure 11:
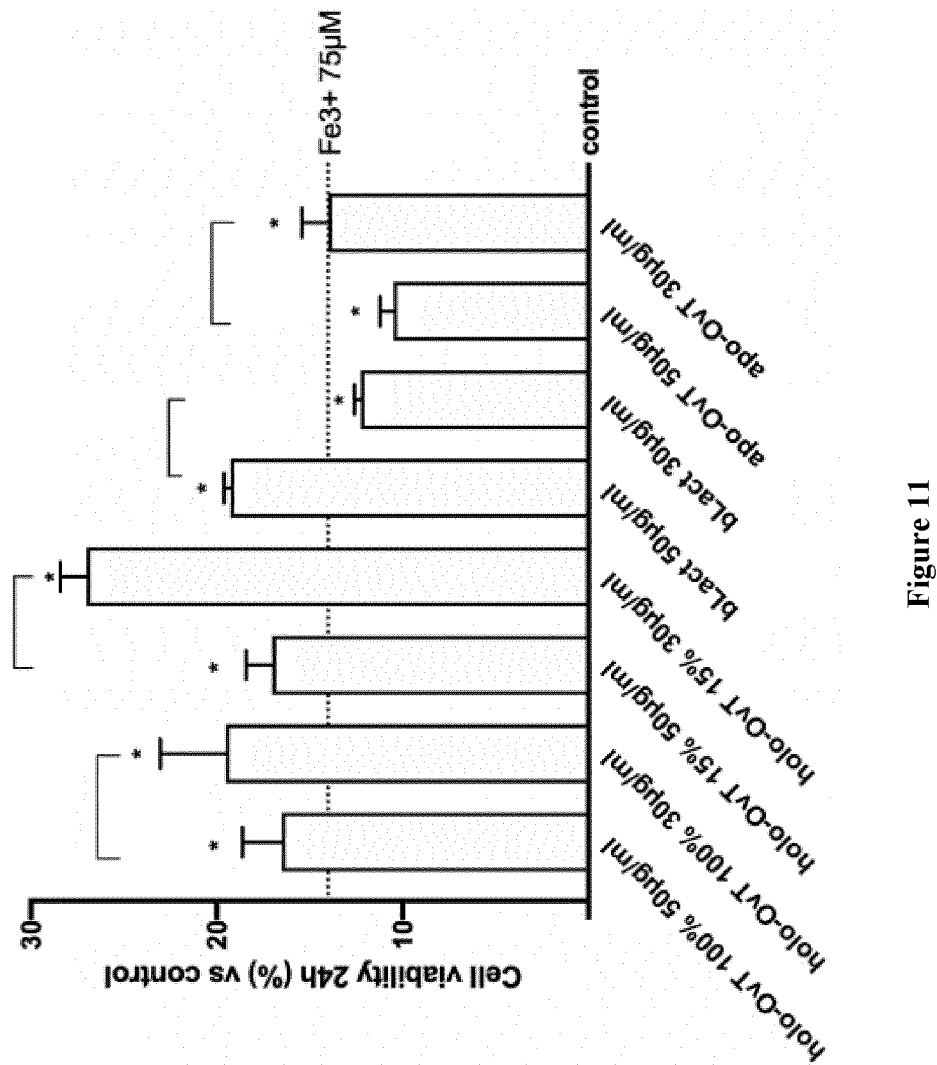
FIG. 11: Cell Viability on CaCo2 cells after treatment with $Fe^{3+}$ in a 3D gastrointestinal model. Data are expressed as +/−SD (%) compared to control of four independent experiments produced in triplicate. *$p<0.05$ vs. control; the horizontal bars are $p<0.05$ vs. the two concentrations tested.

Dose-Response Study of Cell Viability on 3D Gastro-Intestinal Barrier Model in Presence of Iron In this study a 3D gastro-intestinal barrier model has been used as a model mimicking the human complexity in order to evaluate the effects in a complex system and exclude possible adverse reactions. First, a gastro-intestinal barrier model made of a Transwell® transporting set-up have been used, which was also treated with Fe3+ (final concentration 75 µM) for 24 h, then followed by treatment with OvT and bLact for 24 h. The results of cell viability (FIG. 11) confirmed the data previously observed in separate gastric and intestinal models pre-treated with iron 3+ (p<0.05 vs control) indicating that this complex system can be used for subsequent tests in order to have a better idea of the effects on humans from consumption of such test products in presence of food. The results of these tests confirmed again that holo OvT 15% at the concentration of 30 µg/ml showed best results in term of cell viability respect to holo OvT 100% at the same concentration and also respect to bLact.

Figure 12:
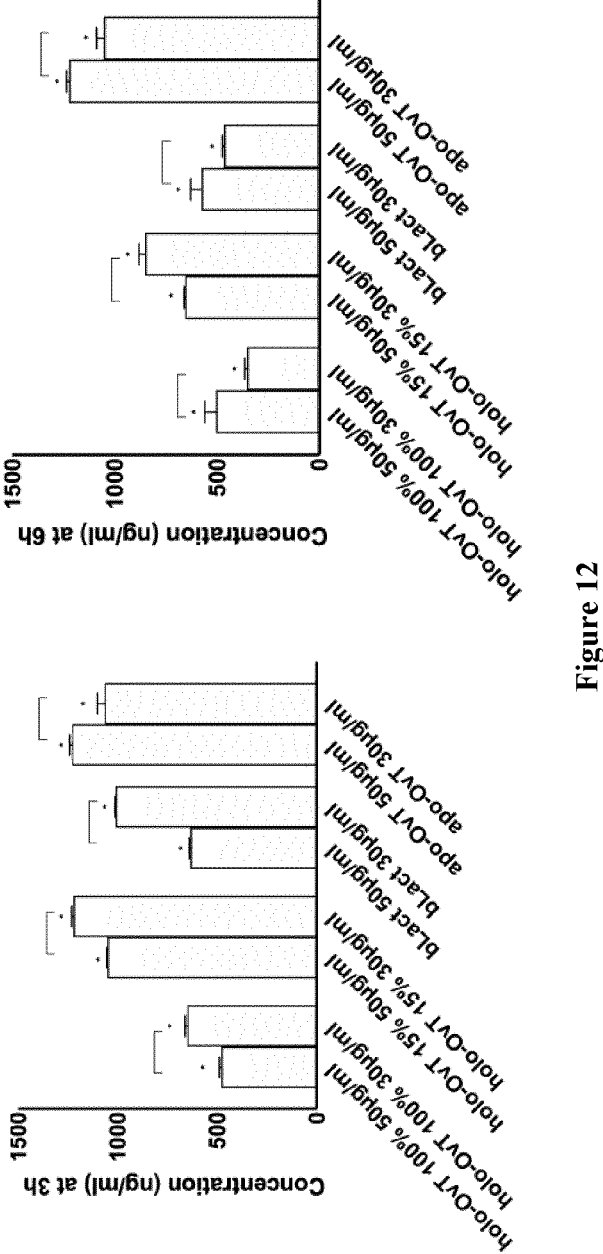
FIG. 12: Total absorption measured at the basolateral level on Transwell® over time after iron stimulation. Gastro-intestinal barrier model is treated with 50 μg/mL and 30 μg/mL of different OvT. Data are expressed as +/−SD (%) compared to control of four independent experiments produced in triplicate. *$p<0.05$ vs. control; the bars are $p<0.05$ vs. the two concentrations tested.

Ovotransferrin Absorption on 3D Gastro-Intestinal Barrier Model in Presence of Iron Having assessed the cell viability with test Products in presence of iron, we have carried out further experiments to study the biological effect of OvT, evaluating its absorption in 3D gastro-intestinal barrier model in the presence of Fe³⁺. The quantitative analysis of the basolateral environment of the gastro-intestinal barrier model confirmed a sustained slow absorption and release over time (3 and 6 hours), confirming the "slow-release effect" (FIG. 12). holo-OvT 15% showed better results, compared to control (p<0,05), and the tested bLact (p<0,05) during the treatment course. The analysis has also confirmed that the lower concentration 30 µg/ml of holo-OvT 15% saturated has a similar effect compared to the higher concentration of 50 µg/ml.

Furthermore, apo-OvT (standard 50 and 30) has shown to be greatly absorbed over the time in presence of iron (p<0.05 vs control, p<0.05 vs tested bLact), suggesting that apo-OvT could be an optimal candidate for administration to human under physiological conditions in presence of food.

Figure 13:
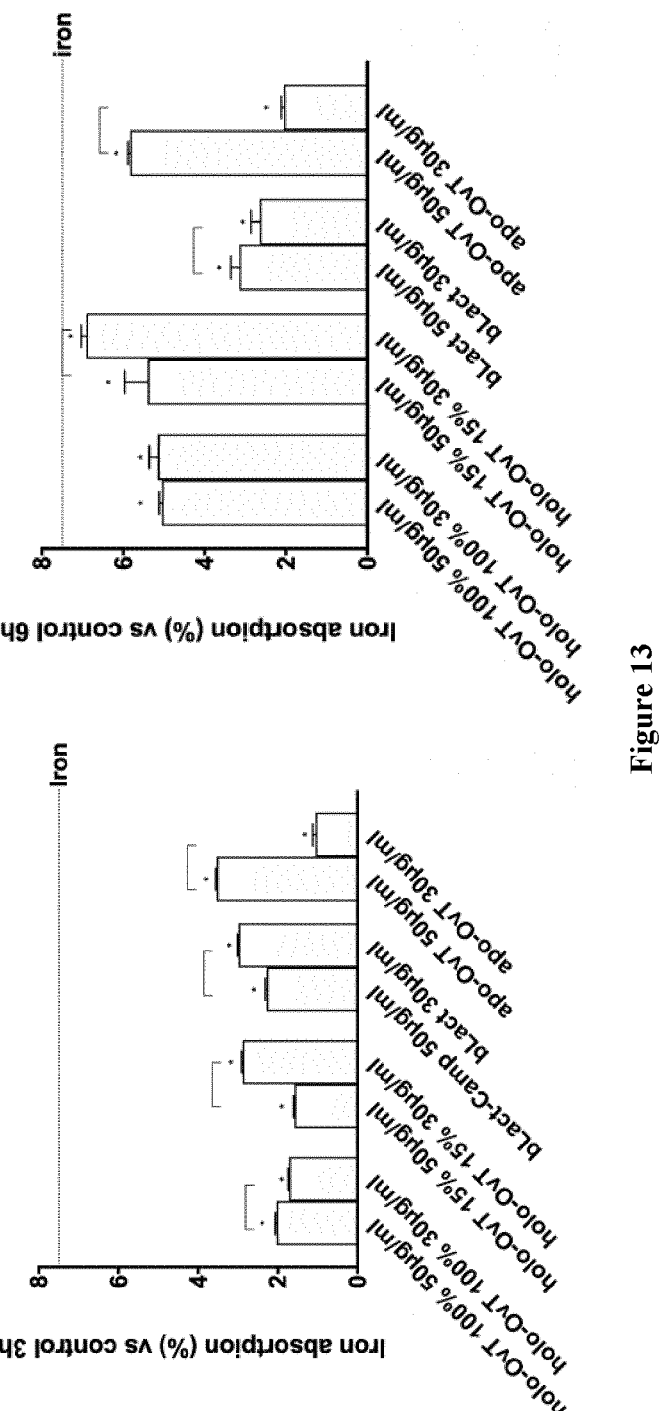
FIG. 13: Total iron absorption measured after iron pre-stimulation. Gastro-intestinal barrier model is treated with 50 μg/mL and 30 μg/mL of different OvT. Data are expressed as +/−SD (%) compared to control of four independent experiments produced in triplicate. *$p<0.05$ vs. control; the horizontal bars are $p<0.05$ vs. the two concentrations tested.

Iron Absorption on 3D Gastro-Intestinal Barrier Model in the Presence of Iron and Ovotransferrin We have further used our gastro-intestinal 3D barrier model pre-treated with iron (Fe³⁺) to check the iron bio-availability and absorption in presence of OvT. The results of quantitative analysis of the basolateral environment (FIG. 13) confirmed that both OvT and bLact are able to sequester iron and to enhsance its bioavailability: this is in direct correlation with the increased absorption of iron over time (3 and 6 hours).

More into details holo-OvT 15% iron saturated at the concentration of 30 µg/ml gave better results in the absorption on the long term (after 6 hours) compared to control (p<0,05) and also respect to bLact (p<0,05). Moreover apo-OvT, particularly at the concentration of 50 µg/ml, showed best results in enhancing the iron bioavailability over time, particularly if compared to the tested bLact (p<0,05).

Analysis of the involved molecular mechanisms on the 3D gastro intestinal barrier model We proceeded with our 3D gastro-intestinal barrier model to check the expression of DMT-1, ferritin, and ferroportin in order to have a complete image of what would happen in humans.

DMT-1

Figure 14:
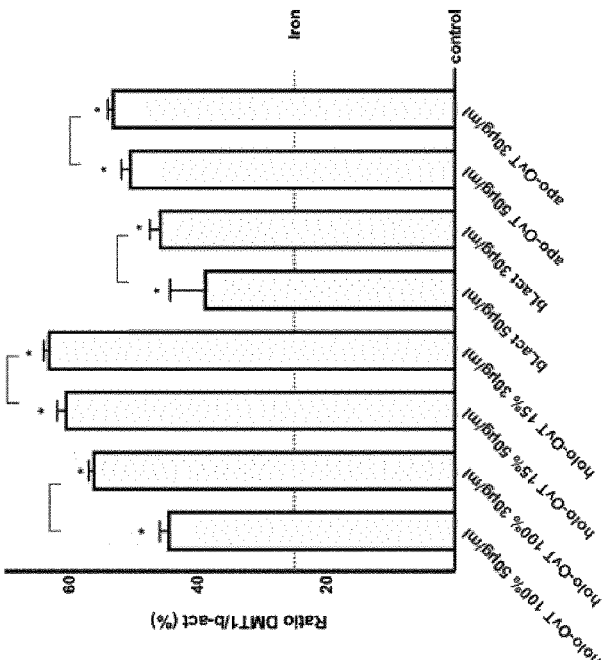
FIG. 14: Densitometric analysis of DMT1 on 3D gastro-intestinal barrier (A; GTL-16; B:Caco2). The results were obtained with normalization on β-act and control, and are expressed as +/−SD (%) compared to control of four independent experiments produced in triplicate. *$p<0.05$ vs. control; the horizontal bars are $p<0.05$ vs. the two concentrations tested.
Figure 14:
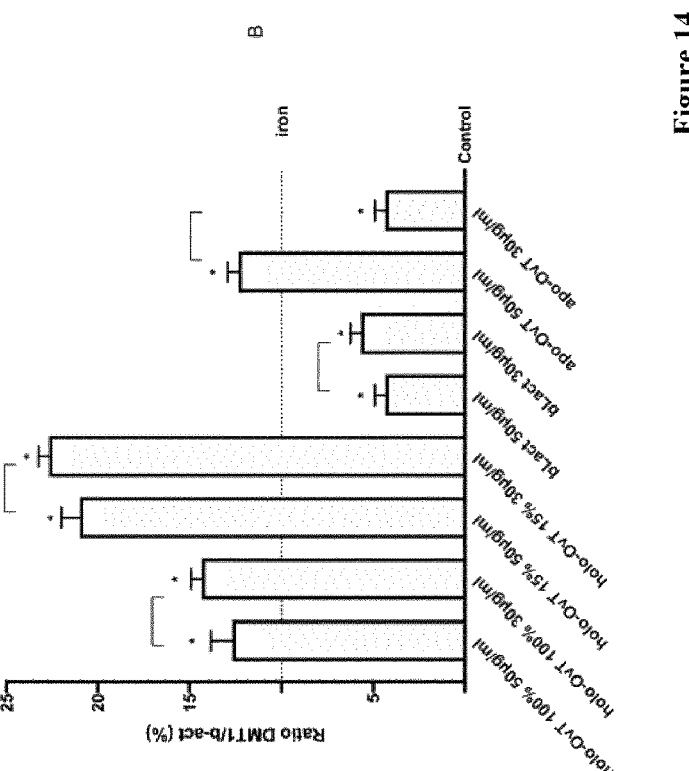

DMT-1 has been tested (densitometric analysis of DMT-1 expression) using the 3D gastro-intestinal barrier model pre-treated with Fe³⁺ (75 µg/ml) followed by 24 h treatments with 50 µg/ml and 30 µg/ml of different OvT products and bLact. DMT-1 expression (FIG. 14) in the gastric part of this model was found to be higher with holo-OvT 15% iron saturated treatment, especially 30 µg/ml compared to control and 50 µg/ml (p<0,05) and to the tested bLact (p<0,05). Also, apo-OvT at the higher concentration 50 µg/ml has shown to enhance the iron absorption in this gastric part more than the tested bLact. In the intestinal part of this model the DMT-1 expression was increased with the all treatments: holo-OvT 15% saturated was anyway the best performing, while apo-OvT has shown to be practically identical to bLact. Iron uptake mechanism using DMT-1 expression was confirmed to be active in both sides (gastric and intestinal), confirming again that OvT and bLact are sharing the same mechanism of iron transport.

Ferritin

Figure 15:
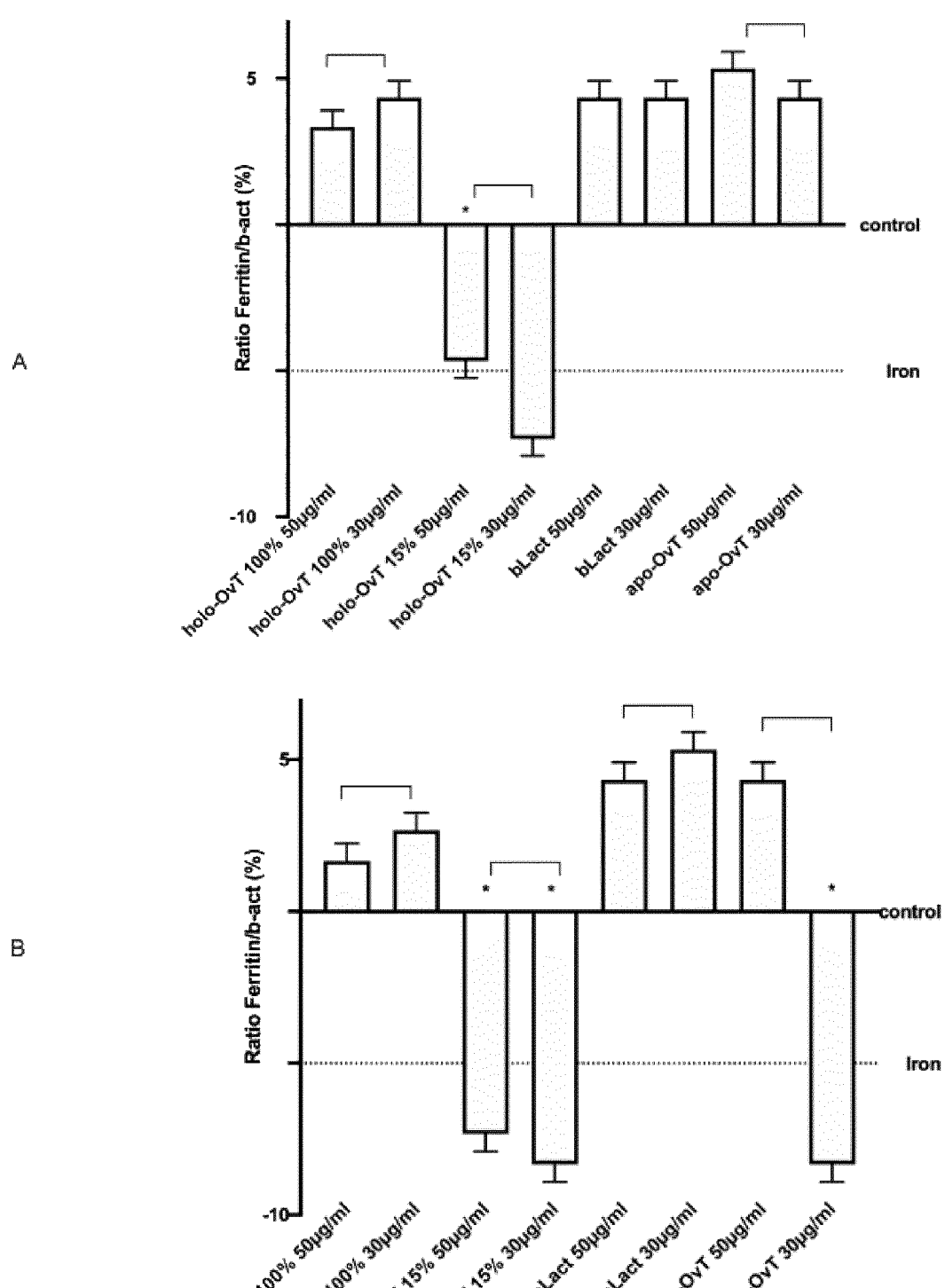
FIG. 15: Densitometric analysis of Ferritin on gastro-intestinal barrier (A; GTL-16; B:Caco2). The results were obtained with normalization on β-act and control, and are expressed as +/−SD (%) compared to control of four independent experiments produced in triplicate. *p<0.05 vs. control; the horizontal bars are p<0.05 vs. the two concentrations tested.
Figure 16:
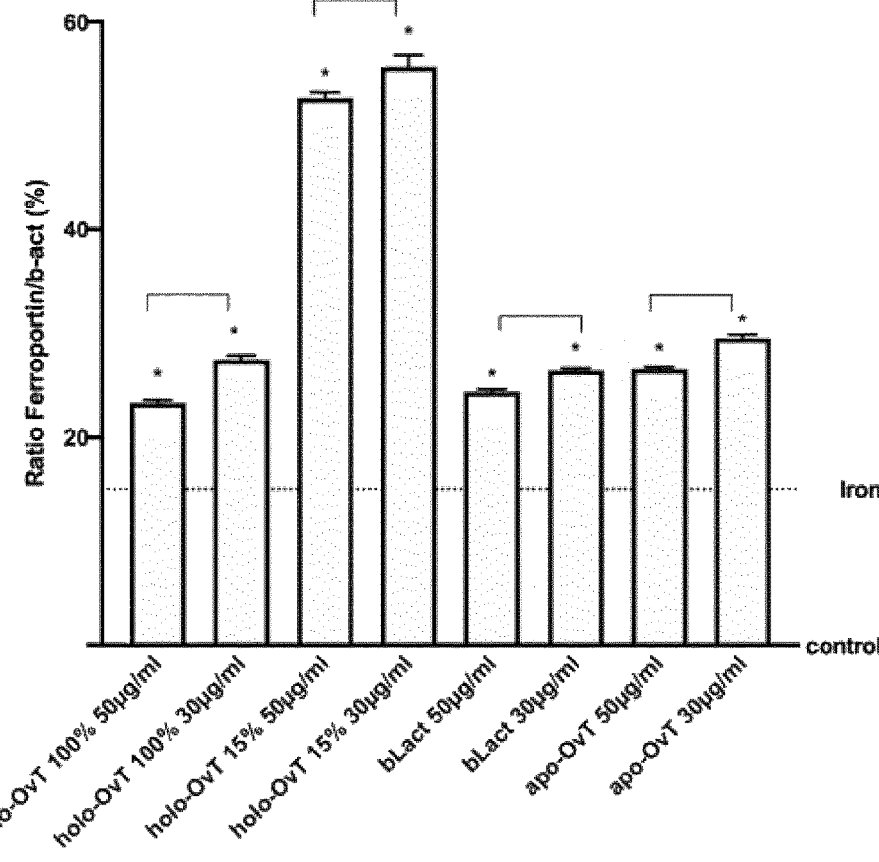
FIG. 16: Densitometric analysis of Ferroportin on gastrointestinal barrier (A; GTL-16; B:Caco2). The results were obtained with normalization on β-act and control, and are expressed as +/−SD (%) compared to control of four independent experiments produced in triplicate. *p<0.05 vs. control; the horizontal bars are p<0.05 vs. the two concentrations.
Figure 16:
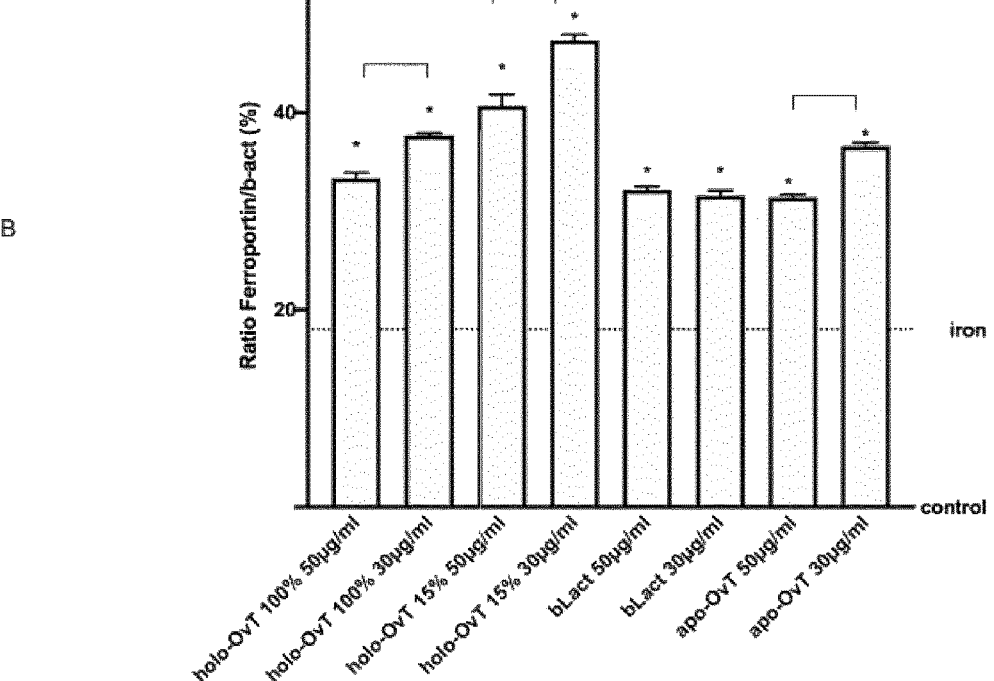

We investigated the ferritin expression in the 3D gastrointestinal barrier model pre-treated with $Fe^{3+}$ (75 μg/ml) followed by 24 h treatments with 50 μg/ml and 30 μg/ml of different OvT products and bLact. The results obtained from both compartments (FIG. 15) have shown that practically there was no ferritin overexpression compared to control, being this a signal of a mechanism, which prevents any form of iron accumulation among all tested products thus excluding gastric and intestinal irritability. Holo-OvT 15% saturated lower concentration of 30 μg/ml has shown to have a comparable effect to its higher concentration 50 μg/ml ($p<0.05$ vs control). Both concentrations have shown to under-express ferritin in both models (gastric and intestinal) compared to control ($p<0.05$), thus excluding gastric and intestinal irritability. Also, apo OvT at the concentration of 30 μg/ml in the intestine showed to under express ferritin Ferroportin Ferroportin is the only known mammalian iron exporter for non-heme iron. After feeding, dietary iron is absorbed into the cells of the small intestine and ferroportin allows that iron to be transported out of those cells and into the bloodstream. After 24 h of iron treatment ($Fe^{3+}$ 75 μg/ml) of gastric-intestinal 3D barrier model followed by treatment with OvT and bLact (FIG. 16), Ferroportin expression has increased during all time of stimulation ($p<0.05$ vs control) for all tested products, confirming an active extrusion mechanism. These results supported the hypothesis of absence of accumulation. More into details a greater transfer across the gastro-intestinal barrier model was observed with holo-OvT 15% saturated 30 μg/ml as a consequence of ferroportin expression, crossing through the gastric and intestinal barrier. holo-OvT 15% saturated 30 μg/ml appeared to be well comparable to its higher concentration 50 μg/ml as well as to the tested bLact ($p<0.05$), demonstrating its effects on iron metabolism in a better way compared to other products. This study also confirmed that apo-OvT gave comparable results respect to bLact.

The invention claimed is:

1. A method of treating iron deficiency and iron deficiency anaemia in a subject in need thereof, said method comprising administering to said subject a pharmaceutical effective amount of ovotransferrin with an iron content from 1 ppm to 246 ppm.

2. The method according to claim 1, wherein said ovotransferrin has an iron content from 1 to 10 ppm.

3. The method according to claim 1, wherein said ovotransferrin has an iron content from 20 ppm to 246 ppm.

4. The method according to claim 3, wherein said ovotransferrin has an iron content of 221-227 ppm.

5. The method according to claim 1 wherein ovotransferrin is administered at a daily dose ranging from 100 to 400 mg in a single dose or twice a day.

* * * * *